United States Patent [19]

Suzuki

[11] Patent Number: 5,594,163

[45] Date of Patent: Jan. 14, 1997

[54] FUEL MIXING RATIO DETECTING DEVICE

[75] Inventor: Hiroyoshi Suzuki, Himeji, Japan

[73] Assignee: Mitsubishi Denki Kabushiki Kaisha, Tokyo, Japan

[21] Appl. No.: 436,763

[22] Filed: May 8, 1995

[30] Foreign Application Priority Data

May 12, 1994 [JP] Japan ................................. 6-98650

[51] Int. Cl.$^6$ ............................................. G01R 27/26
[52] U.S. Cl. .................................. 73/61.44; 73/61.61
[58] Field of Search ........................... 73/23.31, 23.32, 73/61.41, 61.43, 61.44, 61.61, 113, 117.2, 118.1, 119 A

[56] References Cited

U.S. PATENT DOCUMENTS

| | | | |
|---|---|---|---|
| 5,005,402 | 4/1991 | Pischinger et al. | 73/61.43 |
| 5,033,293 | 7/1991 | Honma et al. | 73/61.43 |
| 5,119,671 | 6/1992 | Kopera | 73/61.41 |
| 5,134,381 | 7/1992 | Schmitz et al. | 73/61.41 |
| 5,150,683 | 9/1992 | Depa et al. | 73/116 |
| 5,179,926 | 1/1993 | Ament | 73/61.43 |
| 5,182,523 | 1/1993 | Ertel et al. | 73/61.43 |
| 5,182,942 | 2/1993 | Hartel et al. | 73/61.61 |
| 5,196,801 | 3/1993 | Nogami et al. | 73/61.43 |
| 5,261,270 | 11/1993 | Gonze et al. | 73/61.43 |
| 5,313,168 | 5/1994 | Ogawa | 73/61.43 |
| 5,331,845 | 7/1994 | Bals et al. | 73/61.43 |
| 5,337,017 | 8/1994 | Ogawa | 73/61.43 |
| 5,337,018 | 8/1994 | Yamagishi | 73/61.43 |
| 5,343,156 | 8/1994 | Johnson et al. | 73/61.43 |
| 5,363,314 | 11/1994 | Kobayashi et al. | 73/61.41 |
| 5,367,264 | 11/1994 | Brabetz | 73/61.43 |
| 5,389,884 | 2/1995 | Nakamura et al. | 73/61.41 |
| 5,414,367 | 5/1995 | Ogawa | 73/61.44 |
| 5,414,368 | 5/1995 | Ogawa et al. | 73/61.43 |
| 5,416,425 | 5/1995 | Mouaici | 73/61.43 |

FOREIGN PATENT DOCUMENTS

| | | |
|---|---|---|
| 62-25246 | 2/1987 | Japan . |
| 62-25248 | 2/1987 | Japan . |
| 2190755 | 7/1990 | Japan . |
| 2213760 | 8/1990 | Japan . |
| 4262249 | 9/1992 | Japan . |

*Primary Examiner*—Richard Chilcot
*Assistant Examiner*—Eric S. McCall
*Attorney, Agent, or Firm*—Sughrue, Mion, Zinn, Macpeak & Seas

[57] ABSTRACT

A fuel mixing ratio detecting device can detect a fuel mixing ratio of a mixed fuel with high precision, regardless of the value of an electric conductivity of the fuel. The device comprises a sensor portion (an LC resonance circuit) having an electrostatic capacity detecting portion for detecting an electrostatic capacity of the fuel, which fills a space between electrodes, and a coil connected in parallel with the electrostatic capacity detecting portion, a voltage-controlled oscillator for generating a high-frequency signal having a predetermined frequency by performing a voltage control operation, a phase comparator for detecting a phase difference between a voltage and a current of the high-frequency signal applied to the sensor portion A, a target value switching unit for changing a phase difference target value between a first target value of 0° and a second target value other than 0°, a control unit for controlling the voltage control operation of the voltage-controlled oscillator according to a difference between the phase difference detected by the phase comparator and the set target value, and a computing unit for computing a dielectric constant of the fuel from the frequency of the high-frequency signal when the phase difference has the first target value and for computing the electric conductivity of the fuel from an amount of shift between the frequency of a first high-frequency signal when the phase difference has the first target value and the frequency of a second high-frequency signal when the phase difference has the second target value and for detecting the mixing ratio of the fuel from the computed dielectric constant and the computed electric conductivity.

10 Claims, 14 Drawing Sheets

FREQUENCY f

FUEL MIXING RATIO DETECTING DEVICE

BACKGROUND OF THE INVENTION

1. Field of the Invention

This invention generally relates to a device for detecting a ratio of an admixture or ingredient to a fuel mixture or mixed fuel to be supplied to an internal combustion engine or the like, and more particularly to a fuel mixing ratio detecting device for measuring a mixing ratio of alcohol to alcohol blended gasoline to be used in an automotive engine or the like.

2. Description of the Related Art

In recent years, in many countries such as the United States of America, European countries, Brazil, etc., alcohol blended gasoline has been introduced as a mixed fuel to be used in motor vehicles with the intention of reducing oil consumption and air pollution due to exhaust emissions of motor vehicles. When alcohol blended gasoline is used in an engine matched to an air fuel ratio of normal or non-blended gasoline, it becomes difficult to operate the engine. This is because the stoichiometric air fuel ratio of alcohol is smaller than that of gasoline and as a result, the air fuel ratio of alcohol blended gasoline becomes close to that of a lean mixture. Thus, the alcohol mixing ratio of the alcohol to the alcohol blended gasoline is first detected. Then, the air fuel ratio, the ignition timing and so on are controlled according to the detected alcohol mixing ratio.

A conventional device for detecting such a mixing ratio of the alcohol to the alcohol blended gasoline is disclosed in, for example, Japanese Patent Laid-Open No. 2-190755. This conventional device detects the dielectric constant $\epsilon$ of alcohol blended gasoline or fuel, namely, the alcohol mixing ratio thereof by utilizing a difference between the dielectric constant $\epsilon_g$ of gasoline ($\epsilon_g=2$) and that $\epsilon_m$ of alcohol (incidentally, methanol in this case ($\epsilon_m=33$)), namely, by first placing electrodes in the alcohol blended gasoline and thereafter measuring the electrostatic capacity between the electrodes.

FIG. 19 is a sectional diagram of an electrostatic capacity detecting portion C employed in the conventional device. In this figure, reference numeral 35 designates a metallic cylindrical housing which has a fuel inlet 33a and a fuel outlet 33b formed at opposite ends thereof, respectively. In this cylindrical housing (hereunder referred to simply as a housing) 35, a metallic internal electrode 31 is placed in such a manner that the longitudinal axis of the electrode 31 is coincident with that of the housing 35. A fuel passage is formed between the housing 35 and the internal electrode 31. Further, an electrode lead 36, around which a fuel seal 34 is wound, is connected to the internal electrode 31. Materials having high electric resistances are used for the housing 35, the internal electrode 31, the electrode lead 36 and the fuel seal 34. The internal electrode 31 and the housing 35 cooperate to form a capacitor. The electrostatic capacity $C_f$ of this capacitor changes according to the dielectric constant $\xi$ of the fuel which flows through the fuel passage formed between the internal electrode 31 and the housing 35.

The conventional device forms an LC parallel resonance circuit comprising a coil L and the capacitor C, which has an electrostatic capacity $C_f$, by connecting the coil L to the electrostatic capacity $C_f$ in parallel with each other as an equivalent circuit illustrated in FIG. 20.

The dielectric constant s of fuel can be detected by detecting the resonance frequency of the LC parallel resonance circuit. In the case of the LC parallel resonance circuit of FIG. 20, the resonance frequency $f_0$ thereof is obtained by the following equation (1):

$$f_0 = 1/\sqrt{2\pi\{L(C_f+C_p)\}} \tag{1}$$

where L denotes the reactance of the coil; $C_f$ the electrostatic capacity between the internal electrode 31 and the housing 35; $C_p$ the sum of the floating capacity of the capacitor and the adjusting resistance of the LC parallel resonance circuit.

FIG. 21 shows the resonance-frequency versus methanol-mixing-ratio characteristic of the electrostatic capacity detecting portion C in the case of using methanol blended gasoline. As indicated by the curve $C_h$, with increase in the methanol mixing ratio, the resonance frequency $f_0$ monotonously decreases. For the simplicity of configuration, a back coupling oscillator, a Colpitts oscillator, a Hartley oscillator or the like is usually used as a circuit for detecting the methanol mixing ratio, so as to cause a parallel oscillation. Subsequently, the methanol mixing ratio is detected from an output signal of a frequency divider which divides the resonance frequency $f_0$ of a signal obtained at the parallel oscillation, or from an output signal of a frequency-to-voltage (F/V) converter which performs a frequency-to-voltage conversion on the signal having the resonance frequency $f_0$.

In the conventional methanol mixing ratio detecting device, an LC parallel resonance circuit is formed by connecting a coil to an electrostatic capacity detecting portion in parallel with each other. Further, the resonance frequency of this resonance circuit is obtained to thereby detect the dielectric constant of fuel, namely, the methanol mixing ratio. Methanol, however, has an affinity for water. Therefore, moisture is easily mixed into methanol blended gasoline. Thus, there is the possibility that the electric conductivity thereof increases in a region having a high methanol mixing ratio owing to the presence of various kinds of salts and ions mixed into the moisture.

Accordingly, in the region having a high methanol mixing ratio, with increase in electric conductivity of the methanol blended gasoline, there occurs a decrease in value of the resistance $R_f$ connected in parallel with the capacitor having the electrostatic capacity $C_f$ in the equivalent circuit of FIG. 20, thereby promoting the increase in the electric conductivity. Moreover, the Q-factor of the LC parallel resonance circuit decreases. Consequently, the conventional device fails to meet the oscillation condition. Thus, the conventional device has a problem that in such a case, the oscillation stops and it becomes unable to measure the resonance frequency.

Furthermore, even if the oscillation of the LC parallel resonance circuit does not stop, the oscillation thereof becomes unstable and the dielectric constant of water becomes large ($\epsilon=80$). Thus, as indicated by the curve $C_l$ in FIG. 21, the values of the resonance frequency corresponding to the methanol mixing ratio are shifted from those indicated by the curve $C_h$. Consequently, the conventional device has another problem that in this case, the methanol mixing ratio can not be achieved precisely.

A method for compensating an error in measurement of the methanol mixing ratio has been proposed and described in the Japanese Patent Laid-Open No. 2-213760/1990, in which the electric conductivity of the fuel is measured by providing another detecting electrode having a reduced electrode area and an increased resistance $R_f$ in an electrostatic capacity detecting portion and thereafter the alcohol mixing ratio is calculated from the measured electric conductivity and dielectric constant. This method, however, has drawbacks or problems in that it is necessary to provide the additional electrode in a housing and that thus the structure of a seal becomes complicated and the reliability of the electrostatic capacity detecting portion is deteriorated and the size thereof becomes large.

SUMMARY OF THE INVENTION

Accordingly, the present invention is intended to resolve the aforementioned problems encountered with the conventional device and method referred to above.

An object of the present invention is to provide a fuel mixing ratio detecting device which can detect an alcohol mixing ratio of alcohol to a fuel mixture with high accuracy regardless of the value of the electric conductivity of the fuel mixture.

In accordance with a first aspect of the present invention, there is provided a fuel mixing ratio detecting device comprising: an LC resonance circuit having an electrostatic capacity detecting portion for detecting an electrostatic capacity of fuel and means electrically equivalent to a coil connected in parallel with the electrostatic capacity detecting portion; a phase lock circuit having a voltage-controlled oscillator for generating a high-frequency signal having a frequency determined by a control voltage and for applying the generated high-frequency signal to the LC resonance circuit, a phase comparator for detecting a phase difference between a voltage and a current of the high-frequency signal applied to the LC resonance circuit, and a control unit for controlling the control voltage supplied to the voltage-controlled oscillator according to a difference between the phase difference detected by the phase comparator and a preliminarily set phase-difference target value; target value switching means for changing the phase difference target value between a first target value and a second target value different from the first target value to thereby set the changed target value in the control unit; dielectric-constant computing means for computing a dielectric constant of the fuel on the basis of a first control output of the phase lock circuit after the phase-difference target value is changed to the first target value by the target value switching means; electric-conductivity computing means for computing an electric conductivity of the fuel on the basis of an amount of shift between the first control output, which is outputted from the phase lock circuit after the phase-difference target value is changed to the first target value by the target value switching means, and a second control output, which is outputted from the phase lock circuit after the phase-difference target value is changed to the second target value by the target value switching means; and mixing-ratio detecting means for detecting a fuel mixing ratio of the fuel from the computed dielectric constant and the computed electric conductivity.

Thus, with the configuration described just hereinabove, this fuel mixing ratio detecting device has advantages in that even when the electric conductivity σ decreases, the oscillation never becomes unstable and that the fuel mixing ratio can be detected accurately and easily without providing an additional electrode dedicated to the detection of the electric conductivity.

Further, in accordance with a second aspect of the present invention, there is provided a fuel mixing ratio detecting device comprising: an LC resonance circuit having an electrostatic capacity detecting portion for detecting an electrostatic capacity of fuel and means electrically equivalent to a coil connected in parallel with the electrostatic-capacity detecting portion; a phase lock circuit having a voltage-controlled oscillator for generating a high-frequency signal having a frequency determined by a control voltage and for applying the generated high-frequency signal to the LC resonance circuit, a phase comparator for detecting a phase difference between a voltage and a current of the high-frequency signal applied to the LC resonance circuit, and a control unit for controlling the control voltage supplied to the voltage-controlled oscillator according to a difference between the phase difference detected by the phase comparator and a preliminarily set phase-difference target value; target value switching means for changing a phase difference target value between a first target value and a second target value different from the first target value and for setting the changed target value in the control unit; dielectric-constant computing means for computing a dielectric constant of the fuel on the basis of the frequency of a first high-frequency signal generated by the voltage-controlled oscillator after the phase-difference target value is changed to the first target value by this target value switching means; electric-conductivity computing means for computing an electric conductivity of the fuel on the basis of an amount of frequency shift between a frequency of the first high-frequency signal, which is generated by the voltage-controlled oscillator after the phase-difference target value is changed to the first target value by the target value switching means, and a frequency of a second high-frequency signal, which is generated by the voltage-controlled oscillator after the phase-difference target value is changed to the second target value by the target value switching means; and mixing-ratio detecting means for detecting a fuel mixing ratio of the fuel from the computed dielectric constant and the computed electric conductivity.

Thus, in the case of this fuel mixing ratio detecting device, both of the dielectric constant and the electric conductivity are computed only by simply changing the target value of the phase difference. Consequently, this fuel mixing ratio detecting device is advantageous in that the precision in the measurement of the mixing ratio can be improved by directly measuring the frequency of the high-frequency signal which is applied to the LC resonance circuit.

Moreover, in accordance with a third aspect of the present invention, there is provided a fuel mixing ratio detecting device comprising: an LC resonance circuit having an electrostatic capacity detecting portion for detecting an electrostatic capacity of fuel and means electrically equivalent to a coil connected in parallel with the electrostatic capacity detecting portion; a phase lock circuit having a voltage-controlled oscillator for generating a high-frequency signal having a frequency determined by a control voltage and for applying the generated high-frequency signal to the LC resonance circuit, a phase comparator for detecting a phase difference between a voltage and a current of the high-frequency signal applied to the LC resonance circuit, and a control unit for controlling the control voltage supplied to the voltage-controlled oscillator according to a difference between the phase difference detected by the phase comparator and a preliminarily set phase-difference target value; target value switching means for changing a phase difference target value between a first target value and a second target value different from the first target value and for setting the changed target value in the control unit; dielectric-constant computing means for computing a dielectric constant of the fuel on the basis of a first control voltage applied by the control unit to the voltage-controlled oscillator after the phase-difference target value is changed to the first target value by this target value switching means; electric-conductivity computing means for computing an electric conductivity of the fuel on the basis of an amount of shift between the first control voltage, which is applied by the control voltage to the voltage-controlled oscillator after the phase-difference target value is changed to the first target value by this target value switching means, and a second control voltage, which is applied by the control unit to the voltage-controlled oscillator after the phase-difference target value is changed to the second target value by the target value switching means; and mixing-ratio detecting means for detecting a fuel mixing ratio of the fuel from the computed dielectric constant and the computed electric conductivity. second target value by the target value switching means, and mixing-ratio detecting means for detecting the fuel mixing ratio of the fuel from the computed dielectric constant and the computed electric conductivity.

Thus, in the case of this fuel mixing ratio detecting device, both of the dielectric constant and the electric conductivity are computed by directly using the control voltage to be applied to the control unit and also directly using the amount of shift in the control voltage. Consequently, the configuration of a detecting circuit can be simplified, and the cost of manufacture thereof can be reduced.

Furthermore, in accordance with a fourth aspect of the present invention, there is provided a fuel mixing ratio detecting device comprising: an LC resonance circuit having an electrostatic capacity detecting portion for detecting an electrostatic capacity of fuel and means electrically equivalent to a coil connected in parallel with the electrostatic capacity detecting portion; a phase lock circuit having a voltage-controlled oscillator for generating a high-frequency signal having a frequency determined by a control voltage and for applying the generated high-frequency signal to the LC resonance circuit, a phase comparator for detecting a phase difference between a voltage and a current of the high-frequency signal applied to the LC resonance circuit, and a control unit for controlling the control voltage supplied to the voltage-controlled oscillator according to a difference between the phase difference detected by the phase comparator and a preliminarily set phase-difference target value; target value setting means for setting a first target value in the control unit as a phase difference target value; target value modulating means for modulating the first target value by a predetermined modulation amount; dielectric-constant computing means for computing a dielectric constant of the fuel on the basis of a first control output of the phase lock circuit, which corresponds to the first target value; electric-conductivity computing means for computing an electric conductivity of the fuel based on an amount of shift between the first control output of the phase lock circuit, which corresponds to the first target value, and a second control output of the phase lock circuit, which corresponds to the modulated first target value; mixing-ratio detecting means for detecting the fuel mixing ratio of the fuel from the computed dielectric constant and the computed electric conductivity.

Thus, in the case of this fuel mixing ratio detecting device, the mixing ratio of the fuel is detected by measuring both of the dielectric constant and the electric conductivity at the same time without changing the phase-difference target value. Thus, this fuel mixing ratio detecting device is advantageous in that the operation of detecting the mixing ratio can be achieved quickly.

Additionally, in accordance with a fifth aspect of the present invention, there is provided a fuel mixing ratio detecting device comprising: an LC resonance circuit having an electrostatic capacity detecting portion for detecting an electrostatic capacity of fuel and means electrically equivalent to a coil connected in parallel with the electrostatic capacity detecting portion; a phase lock circuit having a voltage-controlled oscillator for generating a high-frequency signal having a frequency determined by a control voltage and for applying the generated high-frequency signal to the LC resonance circuit, a phase comparator for detecting a phase difference between a voltage and a current of the high-frequency signal applied to the LC resonance circuit, and a control unit for controlling the control voltage supplied to the voltage-controlled oscillator according to a difference between the phase difference detected by the phase comparator and a preliminarily set phase-difference target value; target value setting means for setting a first target value in the control unit as a phase difference target value; target value modulating means for modulating the first target value by a predetermined modulation amount; dielectric-constant computing means for computing a dielectric constant of the fuel on the basis of a frequency of a high-frequency signal generated by the voltage-controlled oscillator correspondingly to the first target value; electric-conductivity computing means for computing an electric conductivity of the fuel based on an amount of shift between the frequency of the high-frequency signal of the phase lock circuit, which corresponds to the first target value, and the frequency of the modulated high-frequency signal; and mixing-ratio detecting means for detecting the fuel mixing ratio of the fuel from the computed dielectric constant and the computed electric conductivity.

Thus, in the case of this fuel mixing ratio detecting device, both of the dielectric constant and the electric conductivity are computed at the same time, so the frequency of the high-frequency signal to be applied to the LC resonance circuit is directly measured. Consequently, this fuel mixing ratio detecting device is advantageous in that the accuracy of the detection of the mixing ratio can be improved.

Further, in accordance with a sixth aspect of the present invention, there is provided a fuel mixing ratio detecting device comprising: an LC resonance circuit having an electrostatic capacity detecting portion for detecting an electrostatic capacity of fuel and means electrically equivalent to a coil connected in parallel with the electrostatic capacity detecting portion; a phase lock circuit having a voltage-controlled oscillator for generating a high-frequency signal having a frequency determined by a control voltage and for applying the generated high-frequency signal to the LC resonance circuit, a phase comparator for detecting a phase difference between a voltage and a current of the high-frequency signal applied to the LC resonance circuit, and a control unit for controlling the control voltage for the voltage-controlled oscillator according to a difference between the phase difference detected by the phase comparator and a preliminarily set phase-difference target value; target value setting means for setting a first target value in the control unit as a phase difference target value; target value modulating means for modulating the first target value by a predetermined modulation amount; dielectric-constant computing means for computing a dielectric constant of the fuel on the basis of a control voltage applied by the control unit to the voltage-controlled oscillator; electric-conductivity computing means for computing an electric conductivity of the fuel based on an amount of shift between a first control output of the phase lock circuit, which corresponds to the first target value, and a second control output of the phase lock circuit, which corresponds to the modulated first target value; and mixing-ratio detecting means for detecting the fuel mixing ratio of the fuel from the computed dielectric constant and the computed electric conductivity.

Thus, in the case of this fuel mixing ratio detecting device, both of the dielectric constant and the electric conductivity are computed by directly using the control voltage to be applied to the control unit and also directly using the amount of shift in the control voltage. Thereby, the configuration of a detecting circuit can be simplified and moreover, the cost of manufacture thereof can be reduced.

Preferably, dielectric-constant correcting means is further provided for correcting the dielectric constant, which is computed by the dielectric constant computing means, based on the amount of shift. Thus, the fuel mixing ratio is detected by correcting the computed value of the dielectric constant according to an amount of shift in the frequency and an amount of shift in the control voltage. As a result, the accuracy of the detection of the mixing ratio can be improved.

Additionally, in accordance with a seventh aspect of the present invention, there is provided a fuel mixing ratio detecting device comprising: an LC resonance circuit having an electrostatic capacity detecting portion for detecting an electrostatic capacity of fuel and means electrically equivalent to a coil connected in parallel with the electrostatic capacity detecting portion; a phase lock circuit having a voltage-controlled oscillator for generating a high-frequency signal having a frequency determined by a control voltage and for applying the generated high-frequency signal to the LC resonance circuit, a phase comparator for detecting a phase difference between a voltage and a current of the high-frequency signal applied to the LC resonance circuit, and a control unit for controlling the control voltage supplied to the voltage-controlled oscillator according to a difference between the phase difference detected by the phase comparator and a preliminarily set phase-difference target value; target value setting means for setting a first target value in the control unit as a phase difference target value of 0°; dielectric-constant computing means for computing a dielectric constant of the fuel on the basis of a frequency of a high-frequency signal outputted from the voltage-controlled oscillator, which corresponds to the phase difference target value of 0°; impedance detecting means for detecting an impedance of the LC resonance circuit when the phase difference target value is set to 0°; electric-conductivity computing means for computing an electric conductivity of the fuel according to the detected impedance; and mixing-ratio detecting means for detecting a fuel mixing ratio of the fuel from the computed dielectric constant and the computed electric conductivity.

Thus, in the case of this fuel mixing ratio detecting device, the electric conductivity of the fuel is detected from a voltage output of the LC resonance circuit, which varies according to a change in the impedance thereof. Consequently, this fuel mixing ratio detecting device is advantageous in that the fuel mixing ratio can be detected by using a circuit having a relatively simple configuration, in comparison with the device in which the electric conductivity is detected by changing the phase difference target value.

Preferably, dielectric-constant correcting means is further provided for correcting the dielectric constant, which is computed by the dielectric constant computing means, based on the impedance of the LC resonance circuit, which is detected by the impedance detecting means. Even though the dielectric constant is obtained according to the resonance frequency which varies with the electric conductivity, the dielectric constant is corrected based on the impedance of the LC resonance circuit, which is proportional to the reciprocal of the electric conductivity. Consequently, the fuel mixing ratio can be obtained with high precision, regardless of a change in the electric conductivity.

Preferably, applied-signal control means is further provided for changing the signal level of a high-frequency signal, which is applied to the LC resonance circuit, based on an output of the impedance detecting means. Thus, the fuel mixing ratio can be detected accurately even in the case where the resonance frequency of the LC resonance circuit changes according to the electric conductivity which is proportional to the reciprocal of the impedance thereof.

BRIEF DESCRIPTION OF THE DRAWINGS

The above and other objects, features, and advantages of the present invention will become apparent from the following description of preferred embodiments of the invention taken in conjunction with the accompanying drawings in which like reference symbols designate like or corresponding parts throughout several views, and in which.

DETAILED DESCRIPTION OF THE PREFERRED EMBODIMENTS

Hereinafter, preferred embodiments of the present invention will be described in detail by referring to the accompanying drawings.

EMBODIMENT 1

Figure 1:
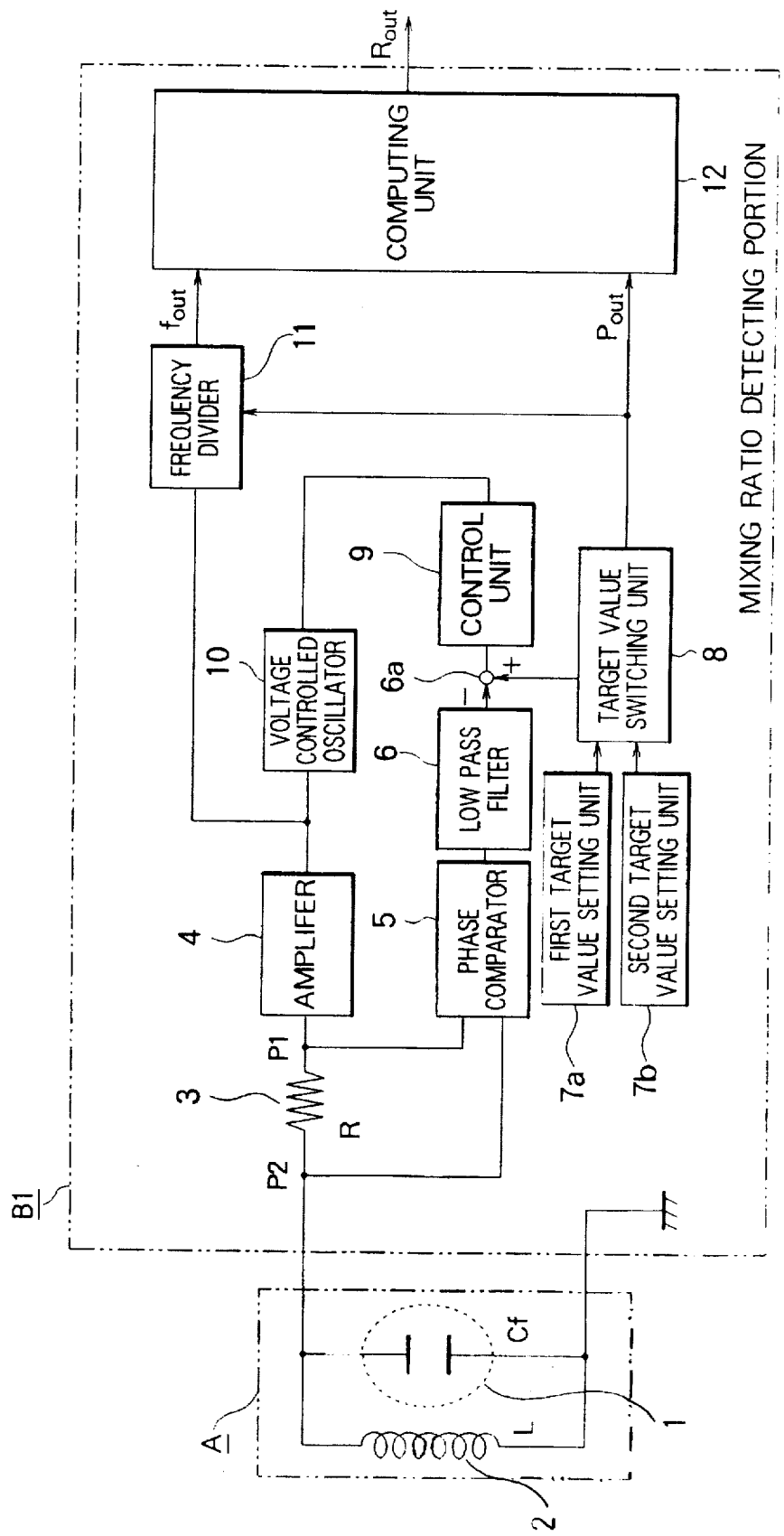
FIG. 1 is a diagram for illustrating the configuration of a first fuel mixing ratio detecting device embodying the present invention, namely, embodiment 1 of the present invention.

Hereunder, a first embodiment (namely, embodiment 1) of the present invention will be described with reference to the drawings. FIG. 1 is a diagram for illustrating the configuration of a fuel mixing ratio detecting device according to this embodiment. In this figure, reference character A designates a sensor portion comprising an electrostatic capacity detecting portion 1, which has an electrostatic capacity $C_f$ determined from the dielectric constant $\epsilon$ of fuel similarly as in the case of the conventional device, and means electrically equivalent to a coil 2 which has a self-inductance L and is connected in parallel with the electrostatic capacity detecting portion 1. Thus, an LC parallel resonance circuit is formed by connecting the electrostatic portion having the electrostatic capacity $C_f$ in parallel with the coil 2 having the self-inductance L. The LC parallel resonance circuit has a terminal, to which a high-frequency signal is applied, and the other terminal which is grounded.

Figure 20:
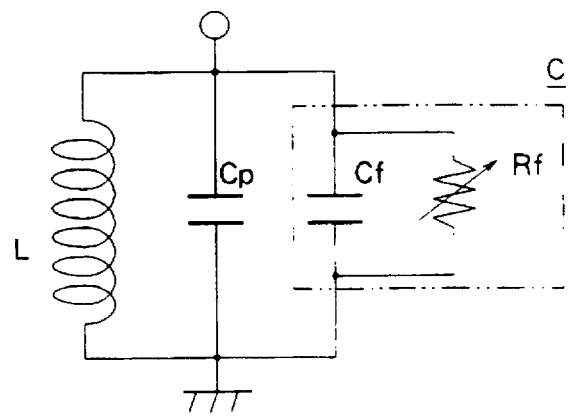
FIG. 20 is a circuit diagram of the equivalent circuit of the electrostatic capacity detecting portion C of the conventional device.
Figure 21:
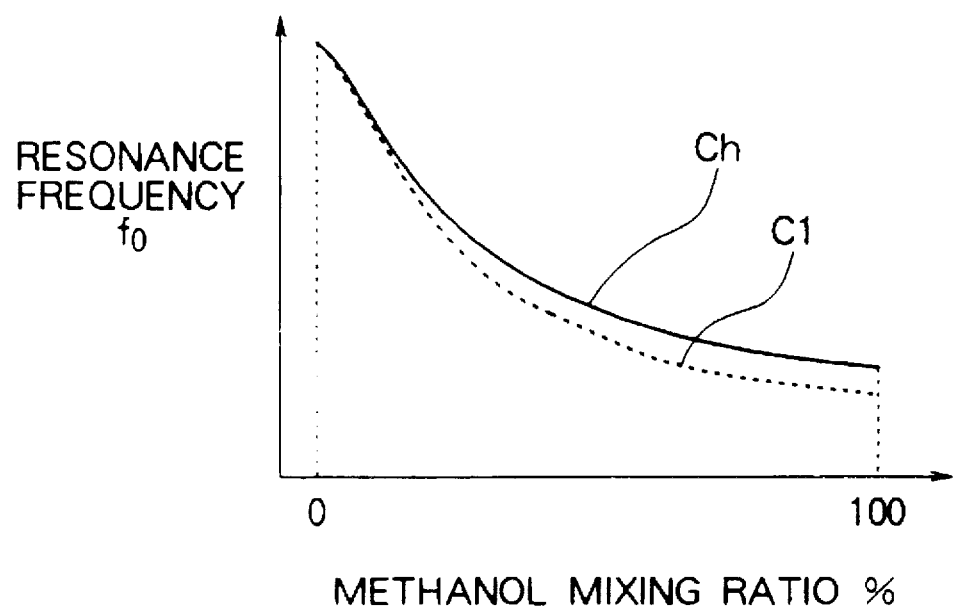
FIG. 21 is a graph for illustrating the resonance-frequency-methanol-mixing-ratio characteristics of the conventional device.

Either of a cored coil and an air-core coil may be used as the coil 2. From the viewpoint of temperature characteristics, an air-core coil is more advantageous. However, from the viewpoint of size, a cored coil is more advantageous. In view of the temperature characteristics of the floating capacity $C_p$ of the coil as illustrated in FIG. 20, in either case, errors in output can be reduced by bring the temperature of the coil 2 as much as close to that of fuel. Therefore, it is preferable that the coil is placed close to the electrostatic capacity detecting portion 1.

Reference character $B_1$ designates a mixing ratio detecting portion which is provided with a resistance 3 connected in series to a terminal of the LC parallel resonance circuit, an amplifier 4 having an output terminal connected through the resistance 3 to the other terminal of the LC parallel resonance circuit, a phase comparator 5 for detecting a difference in phase between the voltage at point $P_1$, which is applied to the entire series circuit comprising the resistance 3 connected to the output terminal of the amplifier 4 and the LC parallel resonance circuit, and the voltage at point $P_2$, which is obtained by dividing the voltage at point $P_1$ into a fraction corresponding to the resistance 3 and the remaining fraction thereof corresponding to the impedance of the LC parallel resonance circuit, and for outputting a phase-difference voltage corresponding to the detected difference in phase, a low-pass filter 6 for averaging the phase-difference voltage outputted from the phase comparator 5 and for outputting the averaged voltage as a DC voltage, a first target setting unit 7a for setting a voltage corresponding to the phase-difference target value of 0° as a first target value 0°, a second target setting unit 7b for setting a voltage corresponding to another phase-difference target value other than the phase-difference value 0° as a second target value $\theta_2$, and a target value switching unit 8 for changing a currently used one of the target values to the other target value.

Incidentally, the comparison between the phases of the voltages at the points $P_1$ and $P_2$ is equivalent to the comparison between the phase of electric current flowing through the LC parallel resonance circuit and the phase of the voltage applied across the LC parallel resonance circuit.

When changed to the first target value, the target value switching unit 8 outputs a timing signal $P_{out}$ having a high signal level H. Further, when changed to the second target value, the target value switching unit 8 outputs a timing signal $P_{out}$ having a low signal level L. Subsequently, the target value outputted from the target value switching unit 8 is compared in an adder 6a with the phase-difference voltage outputted from the low-pass filter 6. Thereafter, a signal representing the result of this comparison is outputted from the adder 6a as a signal representing a deviation voltage.

Moreover, the mixing ratio detecting portion $B_1$ further comprises a control unit 9 for integrating the deviation voltage outputted from the adder 6a and for outputting a corresponding DC control voltage, a voltage-controlled control oscillator 10 for generating a high-frequency signal having a frequency corresponding to the level of the control voltage outputted from the control unit 9 and for applying the generated high-frequency signal to the LC parallel resonance circuit through the amplifier 4 and the resistance 3, a frequency divider 11 to which is inputted the high-frequency signal generated at the time of changing the target value from the voltage-controlled oscillator 10 in synchronization with the changing of the signal level of the timing signal $P_{out}$, and a computing unit 12 for computing a resonance frequency $f_0$, a frequency shift $\Delta$ corresponding to the resonance frequency $f_0$, a dielectric constant $\epsilon$, an electric conductivity $\sigma$ and a methanol mixing ratio and so forth on the basis of the frequency-divided output $f_{out}$ of the frequency divider 11.

Here, it is to be noted that a phase-locked loop (PLL) circuit is composed of the amplifier 4, the phase comparator 5, the low-pass filter 6, the control unit 9 and the voltage-controlled oscillator 10. Further, the computing unit 12 comprises a dielectric computing means, an electric conductivity computing means and a mixing ratio detecting means.

Furthermore, the timing signal $P_{out}$ and the frequency-divided output four are connected to a digital port (not shown) in the computing unit 12. Additionally, reference character $R_{out}$ designates a methanol mixing ratio output from the computing unit 12. In the light of the temperature characteristics of input capacity, it is preferable that the resistance 3 and the phase comparator 5 are placed close to the electrostatic capacity detecting portion C.

Figure 2:
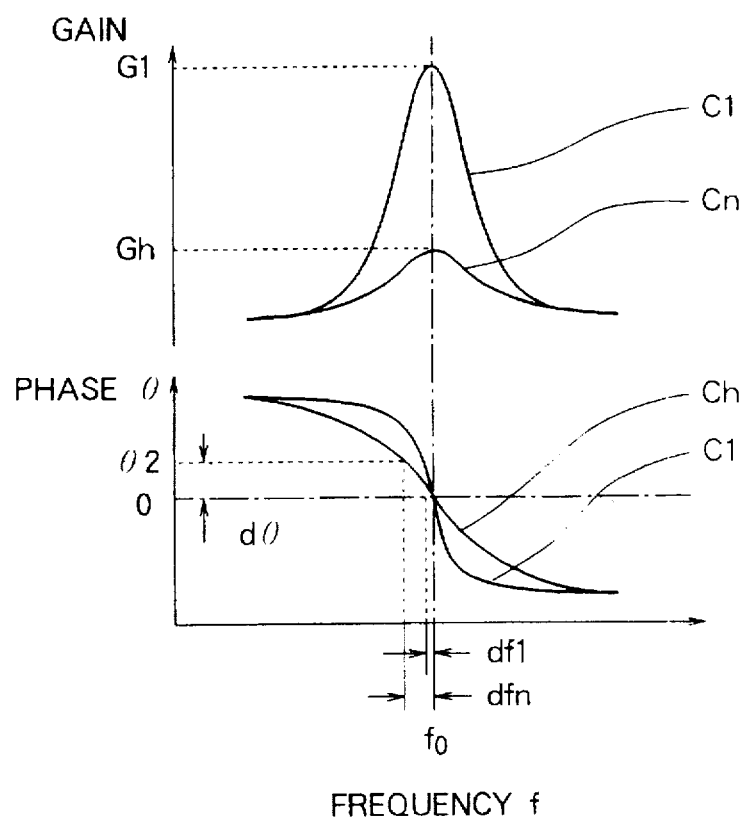
FIG. 2 is a graph for illustrating the frequency characteristics of an LCR series-parallel circuit used in the device of the present invention.

FIG. 2 is a diagram for illustrating graphs which respectively show the gain characteristics concerning the ratio of the voltage at the terminal $P_2$ Of the resistance 3 to the voltage at the other terminal $P_1$ thereof and the phase characteristics concerning the phase difference between signals representing these voltages, in the case of changing the frequency of the high-frequency signal applied to the series circuit, to which the resistance 3 of FIG. 1 and the LC parallel resonance circuit as illustrated in FIG. 20 are connected in series. Incidentally, the gain characteristics of this figure correspond to the impedance characteristics of the LC parallel resonance circuit, and the phase characteristics of this figure correspond to the voltage-current phase characteristics of the LC parallel resonance circuit.

In each of the graphs, the curves $C_l$ and $C_h$ correspond to the case where the electric conductivity $\sigma$ of fuel is low and the case where the electric conductivity $\sigma$ of fuel is high, respectively. When changing the frequency of the high-frequency signal to be applied, there are presented the parallel resonance characteristics in which the gain in each of such cases reaches a maximum value at the parallel resonance frequency $f_0$ at which the difference in phase between the voltage and the electric current of the LC parallel resonance circuit becomes 0°. However, the maximum values $G_h$ and $G_l$ of the gains in such cases are different from each other, depending on the high and low values of the electric conductivity $\sigma$. Further, when the difference between the phases of the voltage and the electric current is made to be $\theta_2$ by shifting the frequency of the signal from the resonance frequency $f_0$, amounts of the shift of the frequency from the resonance frequency $f_0$ respectively corresponding to such cases become $df_h$ and $df_l$ which are different from each other depending on the high and low values of the electric conductivity $\sigma$. These graphs show that the higher the electric conductivity $\sigma$ becomes, the larger is the amount of shift of the frequency from the resonance point at the same phase. Further, the gain G and the phase $\theta$ are given by the following equations (2) and (3), respectively.

$$G = 2\pi f L R / \sqrt{\{R^2 R_f^2 (1 - 4\pi^2 f^2 LC)^2 + 4\pi^2 f^2 L^2 (R+R_f)^2\}} \quad (2)$$

$$\tan\theta = RR_f/(R+R_f) * (1 - 4\pi^2 f^2 LC)/(2\pi f L) \quad (3)$$

where $R_f$ designates the resistance of fuel. Here, let K denote a constant which is determined according to the shape of the electrostatic capacity detecting portion A, then the electric conductivity $\sigma$ is obtained by the following equation:

$$\sigma = 1/KR_f.$$

When only the resistance $R_f$, namely, the electric conductivity $\sigma$ of fuel changes as illustrated in this figure, the resonance frequency $f_0$ is obtained by the aforementioned equation (1) irrespective of the electric conductivity $\sigma$.

Figure 3:
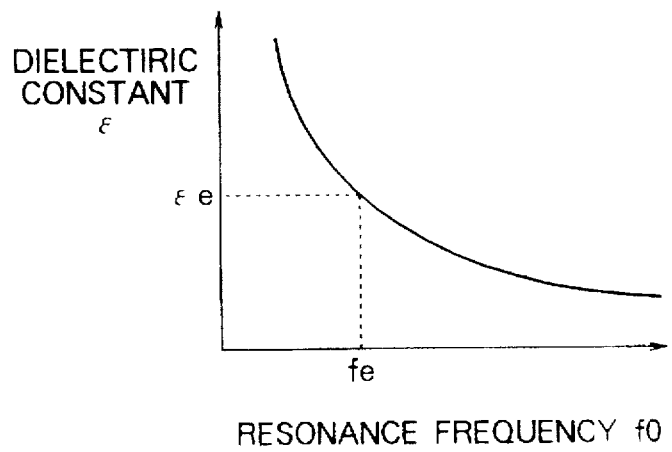
FIG. 3 is a graph for showing the dielectric-constant-resonance-frequency characteristics of fuel.

FIG. 3 is a graph showing the characteristic relation between the dielectric constant of the fuel and the resonance frequency. Further, the dielectric constant $\epsilon$ is given by the following equation (4).

$$\epsilon = 1/V(a+bf_0) \quad (4)$$

where a and b are constants determined by the shape of the sensor A and the inductance L and the floating capacity $C_p$ of the coil.

Further, data, which represents the dielectric constant $\epsilon$ corresponding to the resonance frequency $f_0$, is preliminarily stored in the form represented by the equation (4) or in the form of a $f_0$-$\epsilon$ map in a read-only memory (ROM) (not shown) of the computing unit 12.

Figure 4:
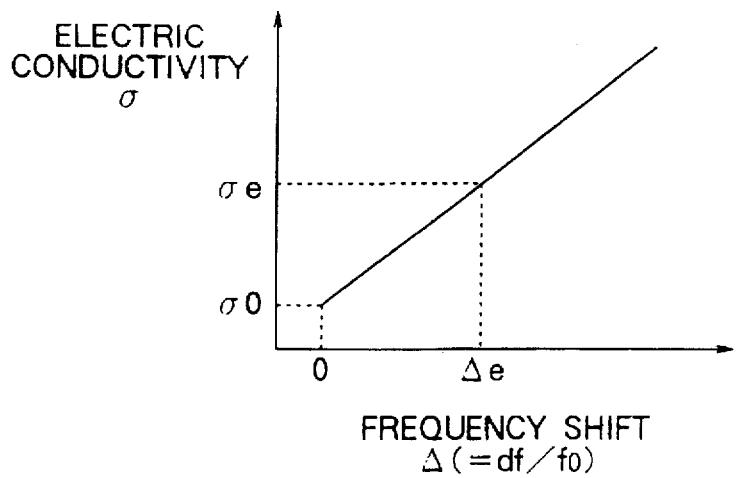
FIG. 4 is a graph for showing the electric-conductivity-frequency-shift characteristics of fuel.

FIG. 4 is a diagram illustrating the relation between the electric conductivity $\sigma$ of fuel and the frequency shift ($=df/f_0$) obtained by normalizing a frequency deviation df by the resonance frequency $f_0$, the frequency deviation df being a difference between the output frequency of the PLL in the case where the target value of the phase difference is the first target value of 0° as illustrated in FIG. 2, namely, the resonance frequency $f_0$, and the frequency thereof in the case where the phase difference is converged upon the second target value $\theta_2$. In the region where the phase $\theta$ is small, the electric conductivity $\sigma$ is expressed by the following equation (5) which is obtained by differentiating the equation (3) with respect to the frequency f.

$$\sigma = 1/K*(G\Delta/\theta_2 + 1/R) \quad (5)$$

where G designates a value determined by the resonance frequency $f_0$ and the inductance L of the coil. The electric conductivity $\sigma$ monotonously increases with increase in the frequency shift $\Delta$ (see the graph of FIG. 4). Data, which represents the dielectric constant $\epsilon$ corresponding to the frequency shift $\Delta$, is preliminarily stored in the form represented by equation (5) above or in the form of a $\Delta$-K$\sigma$ map in the ROM of the computing unit 12.

Figure 5:
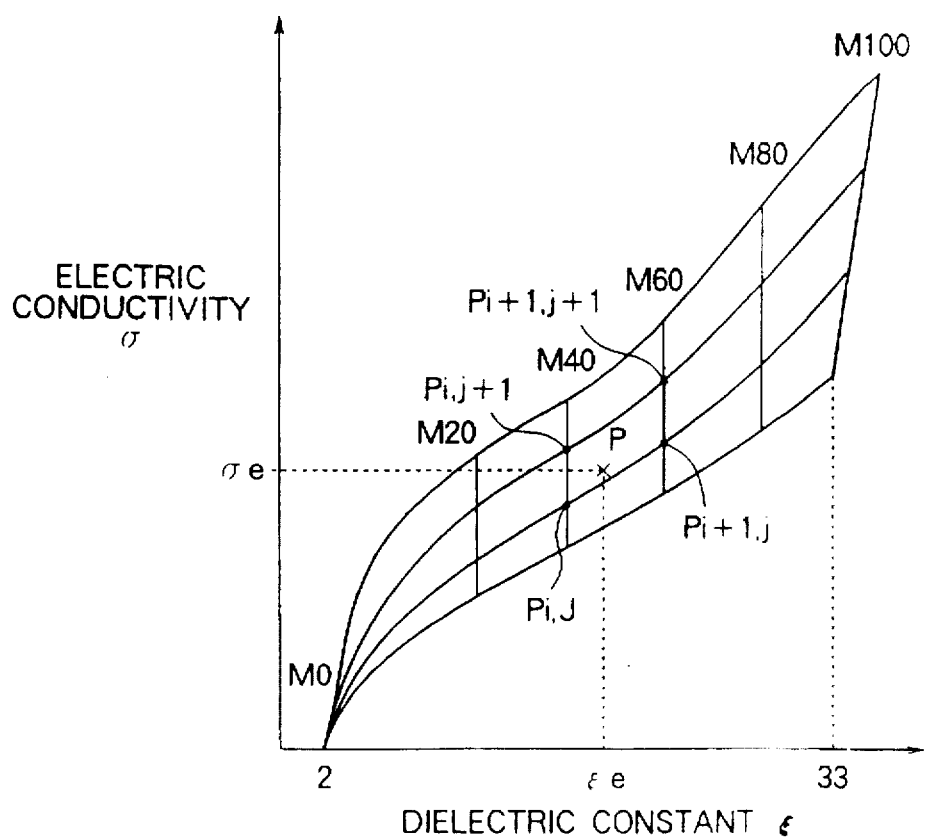
FIG. 5 is a graph for illustrating the characteristic relation among a dielectric constant, an electric conductivity and a methanol mixing ratio.

FIG. 5 is a graph for illustrating the characteristic relation among the dielectric constant $\epsilon$, the electric conductivity $\sigma$ and the methanol mixing ratio M (%) in the case where methanol blended gasoline is used as the fuel. Although the electric conductivity $\sigma$ of methanol alone is large in comparison with that of gasoline, methanol has an affinity for water. Therefore, the fuel tends to contain water as a conductive material.

Consequently, when water is mixed into the fuel mixture, the electric conductivity $\sigma$ thereof increases owing to electrolyte ions contained in water. Moreover, in the case where the same methanol mixing ratio is maintained, the dielectric constant $\epsilon$ of the fuel becomes large due to the large dielectric constant of water ($\epsilon=80$). Data, which represents the relation among the dielectric constant $\epsilon$, the electric conductivity $\sigma$ and the methanol mixing ratio M, is preliminarily stored in the form of a ($\epsilon$, $\sigma$)-M map in the ROM of the computing unit 12.

Next, an operation of this embodiment will be described hereinbelow by referring to each of FIGS. 1 to 5. The high-frequency signal generated and outputted by the voltage-controlled oscillator 10 is amplified by the amplifier 4. Then, the amplified signal is applied to the series circuit comprising the LC parallel resonance circuit, which has a capacitor of the electrostatic capacity $C_l$ due to the dielectric constant $\epsilon$ of the fuel as a circuit element, and the resistance 3. At that time, the phases of the voltages at the terminals $P_1$ and $P_2$ of the resistance 3 are compared with each other by the phase comparator 5. Subsequently, the result of the comparison is outputted therefrom to the low-pass filter 6 as a phase-difference voltage. Then, a DC voltage corresponding to the difference between the phases of the voltage and the electric current of the LC parallel resonance circuit is outputted from the low-pass filter 6 as a signal $\theta$.

The signal $\theta$ is compared in the adder 6a with a signal representing the first target value, which is outputted from the target value switching unit 8. The deviation between these signals is integrated by the control unit 9. Then, the integrated deviation is outputted from the control unit 9 to the voltage-controlled oscillator 10 as a control voltage. The voltage-controlled oscillator 10 controls the oscillation frequency according to the control voltage. The aforementioned operation is repeated until the phase lock is accomplished. Thus, the phase difference is converged upon the first target value 0° (the phase difference θ=0°). Namely, the voltage-controlled oscillator 10 generates and outputs a high-frequency signal having the frequency at which the LC parallel resonance circuit is put into a resonant condition.

After the lapse of a predetermined time, the target value switching unit 8 changes the phase difference target value from the first target value 0° to the second target value $\theta_2$. As a result, the PLL circuit outputs a high-frequency signal, according to which the difference in phase between the voltage signals at both terminals $P_1$ and $P_2$ Of the resistance 3 becomes $\theta_2$, to the LC parallel resonance circuit. At that time, the frequency corresponding to the second target value $\theta_2$ is changed to $(f_0-df)$ as illustrated in FIG. 2.

The target value switching unit 8 outputs a timing signal $P_{out}$ to the frequency divider 11 and the computing unit 12 in synchronization with the change in the phase difference target. When the target value of the phase difference is the first target value 0°, the timing signal $P_{out}$ having the high level H is outputted therefrom. In contrast, when the target value of the phase difference is the second target value $\theta_2$, the timing signal $P_{out}$ having the low level L is outputted therefrom instead of the timing signal $P_{out}$ having the high level H. Then, the frequency divider 11 divides the resonance frequency $f_0$ corresponding to the first target value 0° when the timing signal $P_{out}$ having the high level H is inputted from the target value switching unit 8 thereto. Thereafter, the frequency divider 11 outputs a signal, which is obtained as a result of the frequency division, to the digital input port of the computing unit 12 as a low-frequency signal $f_{out}$.

In the case where the target value of the phase difference is changed by the target value switching unit 8 into the second target value $\theta_2$, the timing signal $P_{out}$ having the low level L is outputted to the frequency divider 11 and the computing unit 12, instead of the timing signal having the high level H. As a consequence, the frequency divider 11 resets the result of the frequency division and divides the frequency of $(f_0-df)$ and outputs a signal, which is obtained as a result of this frequency division, to the digital input port of the computing unit 12 as a low-frequency signal $f_{out}$.

Further, when the timing signal $P_{out}$ having the high level H is inputted, a central processing unit (CPU) of the computing unit 12 measures the resonance frequency $f_0/N$ corresponding to the first target value 0° from the frequency signal $f_{out}$ inputted from the frequency divider 11. When changed to the timing signal $P_{out}$ having the low level L is inputted, the CPU of the computing unit 12 measures the resonance frequency $(f_0-df)/N$ corresponding to the second target value $\theta_2$ from the frequency signal $f_{out}$ inputted from the frequency divider 11. Moreover, the CPU computes the frequency shift $\Delta=df/f_0$, based on both of the frequencies df and $f_0$. Here, it is to be noted that N is the frequency division ratio of the frequency divider 11.

If fuel having an unknown methanol mixing ratio M is now introduced into the sensor portion A, the CPU of the computing unit 12 reads the frequency signal $f_{out}$ and the timing signal $P_{out}$ from the digital input ports and calculates the frequency shift $\Delta_e=df/f_e$ from the resonance frequency $f_e$ (namely, $f_0$) and the frequency deviation df which correspond to this unknown fuel. Next, this CPU computes the dielectric constant $\epsilon_e$ corresponding to the dielectric constant $f_e$ as illustrated in FIG. 3 by using the $f_0$-$\epsilon$ map preliminarily stored in the ROM or by using the equation (4).

Moreover, this CPU computes the electric conductivity $\sigma_e$ corresponding to the frequency shift $\Delta_e$ as illustrated in FIG. 4 by using the $\Delta_e$-$\sigma$ map preliminarily stored in the ROM or by using the equation (5). Finally, this CPU computes the methanol mixing ratio M at the point P from the dielectric constant $\epsilon_e$ and the electric conductivity $\sigma_e$ by using the ($\epsilon$, $\sigma$)-M map preliminarily stored in the ROM. In the case of FIG. 5, the methanol mixing ratio M is calculated or obtained by performing an interpolation operation on the dielectric constant $\epsilon$ and the electric conductivity $\sigma$ corresponding to four points surrounding the point P, namely, $P_{i,j}$ and $P_{i,j+1}$, at which the corresponding methanol mixing ratios are 40%, and $P_{i+1,j}$ and $P_{i+1,j+1}$, at which the corresponding methanol mixing ratios are 60%. A signal representing the obtained methanol mixing ratio M is outputted from an output port (not shown) of the computing unit 12 as an output signal $R_{out}$.

In the case of this embodiment having the aforementioned configuration, a PLL is used as the oscillation circuit. Thus, even when the electric conductivity $\sigma$ decreases similarly as in the case of the conventional device, the oscillation never becomes unstable in the case of this embodiment. Moreover, this embodiment can detect both of the dielectric constant $\epsilon$ and the electric conductivity $\sigma$ only by changing the target value of the phase difference used in the PLL. Consequently, this embodiment has an advantage in that the methanol mixing ratio can be detected accurately and easily without providing the electrode dedicated to the detection of the electric conductivity.

EMBODIMENT 2

Although the aforementioned embodiment 1 computes the dielectric constant $\epsilon$ from the resonance frequency $f_0$ of the LC resonance circuit and further computes the electric conductivity $\sigma$ of the fuel from the amount of the frequency shift $\Delta$ corresponding to this resonance frequency $f_0$ and finally detects the methanol mixing ratio from the computed dielectric constant $\epsilon$ and the computed electric conductivity $\sigma$, the dielectric constant $\epsilon$ may be computed from the output voltage of the control unit 9, which is applied therefrom to the voltage-controlled oscillator 10, without using the frequency signal when the voltage-controlled oscillator 10 outputs the high-frequency signal having the resonance frequency $f_0$ to the LC parallel resonance circuit. Moreover, the electric conductivity $\sigma$ may be computed from this output voltage of the control unit and the amount of shift in the output voltage of the control unit, which corresponds to a change in the target value. Furthermore, the methanol mixing ratio M may be detected from the computed dielectric constant $\epsilon$ and the computed electric conductivity $\sigma$.

Figure 6:
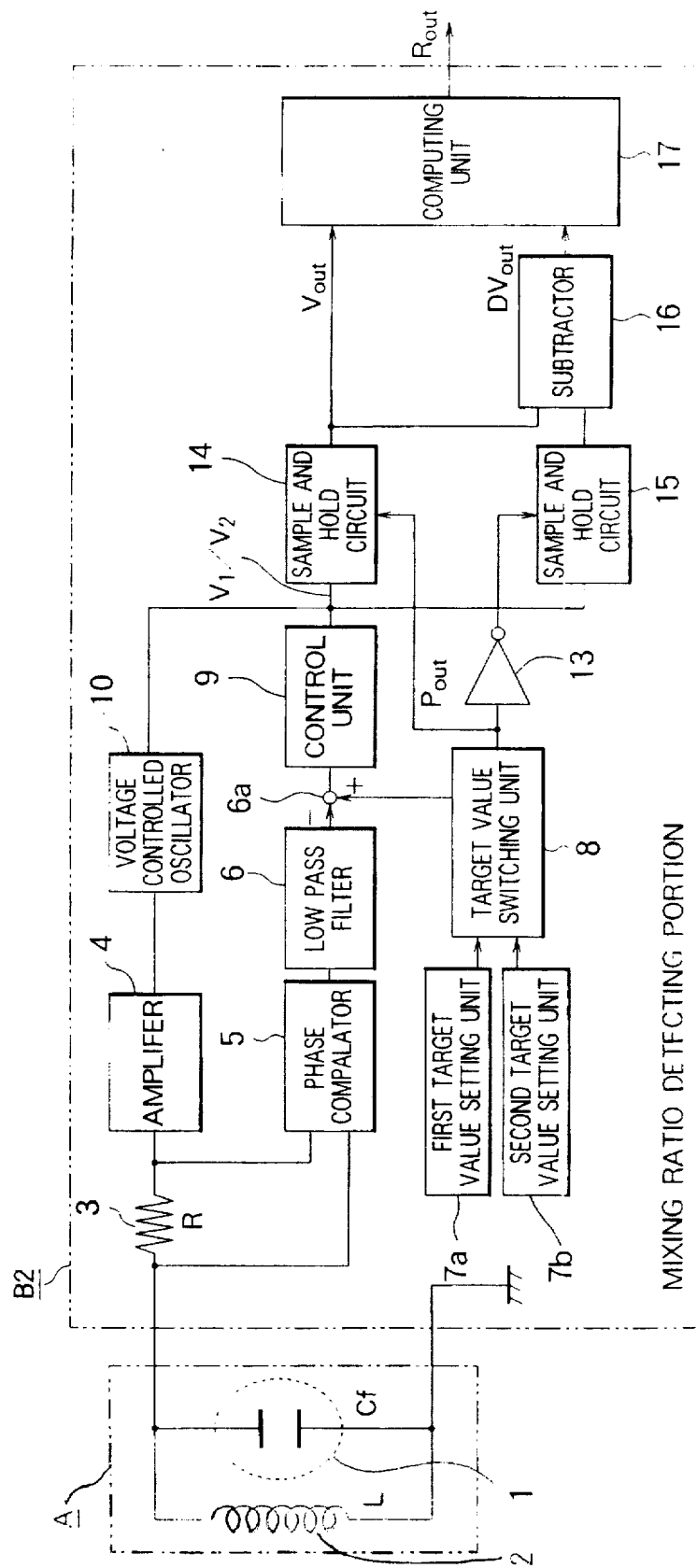
FIG. 6 is a diagram for illustrating the configuration of a second fuel mixing ratio detecting device embodying the present invention, namely, embodiment 2 of the present invention.

FIG. 6 is a diagram illustrating the configuration of a fuel mixing ratio detecting device in accordance with a second embodiment (namely, embodiment 2) of the present invention. Incidentally, like reference symbols designate like or corresponding parts of FIG. 1. In FIG. 6, reference character $B_2$ denotes a mixing ratio detecting portion of this embodiment. The mixing ratio detecting portion $B_2$ is provided with an inverter circuit 13 for inverting the signal level of the timing signal $P_{out}$ when this timing signal is inputted thereto from the target value switching unit 8, and for outputting the inverted signal, a sample-and-hold circuit 14 for holding an output voltage (corresponding to the first target value 0°) of the control unit 9 when the timing signal $P_{out}$ having the high level H is inputted thereto from the target value switching unit 8, a sample-and-hold circuit 15 for holding an output voltage (corresponding to the second target value $\theta_2$) of the control unit 9 when the timing signal $P_{out}$ having the high level H is inverted and the inverted timing signal is inputted thereto, a subtractor 16 for subtracting an output voltage of the control unit 9, which is held by the sample-and-hold circuit 15, from another output voltage of the control unit 9, which is held by the sample-and-hold circuit 14, and for calculating a deviation voltage $DV_{out}$ of the control voltage, and a computing unit 17 containing a CPU. Further, the computing unit 17 converts the output voltage $V_{out}$ of the control unit 9, which is inputted thereto from the sample-and-hold circuit 14 through an analog input port (not shown), to a value corresponding to the resonance frequency $f_0$ and computes the dielectric constant $\epsilon$. Moreover, the computing unit 17 converts the deviation voltage $DV_{out}$ of the control voltage, which is calculated by the subtractor 16, to a value corresponding to the frequency deviation df. Furthermore, the computing unit 17 computes the frequency shift $\Delta_e$ from the resonance frequency $f_0$ and the frequency deviation df and thus calculates the electric conductivity $\sigma$. As the result of the computation and calculation, the computing unit 17 detects the methanol mixing ratio M.

Next, an operation of this embodiment will be described hereinbelow. First, the phase difference target value of the PLL is changed between the first target value 0° and the second target value $\theta_2$ by providing a predetermined timing. When changed to the first target value 0°, the signal level of the timing signal $P_{out}$ is changed or inverted to the high level H. In contrast, when changed to the second target value $\theta_2$, the signal level of the timing signal $P_{out}$ is changed to the low level L.

As a result, when changed to the first target value 0°, the sample-and-hold circuit 14 holds the output voltage $V_1$ outputted from the control unit 9, which corresponds to the resonance frequency $f_0$, and outputs the held voltage to the computing unit 17 as the output voltage $V_{out}$ of the control unit 9. In contrast, when changed to the second target value $\theta_2$, the sample-and-hold circuit 15 holds the output voltage $V_2$ of the control unit 9, which corresponds to the second target value $\theta_2$, in response to the timing signal $P_{out}$, which is inverted by the inverter 13 and has the high level H, and outputs the held voltage to the subtractor 16.

The subtractor 16 subtracts the output voltage $V_{out}$ of the control unit 9, which is inputted thereto from the sample-and-hold circuit 15, from the output voltage $V_{out}$ of the control unit 9, which is inputted thereto from the sample-and-hold circuit 14, and further outputs the resultant deviation voltage $DV_{out}$ to the computing unit 17.

The CPU of the computing unit 17 inputs the output voltage $V_{out}$ of the control unit 9 and the deviation voltage $DV_{out}$ from the analog input port thereof. Further, the CPU converts the output voltage $V_{out}$ to the resonance frequency $f_e$ and also converts the deviation voltage $DV_{out}$ to the frequency deviation df. Thus the CPU obtains the frequency shift $\Delta_e = df/f_e$.

Further, similarly as in the case of embodiment 1, the CPU computes the dielectric constant $\epsilon$ from the resonance frequency $f_e$ and also computes the electric conductivity $\sigma$ from the frequency shift $\Delta_e$ calculated from the frequency $f_e$ and the frequency deviation df. Thus the CPU detects the methanol mixing ratio M from results of such computations. Alternatively, the methanol mixing ratio M may be computed as the result of the dielectric constant s and the electric conductivity $\sigma$ being obtained by using the $V_{out}$-$\epsilon$ map and the $DV_{out}/V_{out}$-$\sigma$ map which are preliminarily stored in the ROM, without converting the output voltage $V_{out}$ and the deviation voltage $DV_{out}$ into frequencies.

Moreover, in the case of this embodiment, the output voltage $V_{out}$ of the control unit 9 and the deviation voltage $DV_{out}$ corresponding to the dielectric constant $\epsilon$ and the electric conductivity $\sigma$ are obtained by using the sample-and-hold circuits 14 and 15 and the subtractor 16 and the obtained output voltage $V_{out}$ and the obtained deviation voltage $DV_{out}$ are then inputted to the computing unit 17. The output voltage of the control unit 9 and the timing output or signal $P_{out}$, however, may be directly inputted to the computing unit 17. Moreover, the dielectric constant $\epsilon$ and the electric conductivity $\sigma$ may be obtained on the basis of the output voltage of the control unit 9 when the timing output $P_{out}$ is inputted thereto.

Namely, an output voltage V of the control unit 9 is inputted to the computing unit 17 through the analog input port thereof (not shown). Moreover, the timing output $V_{out}$ is inputted to the computing unit 17 through the digital input port thereof. Furthermore, after the signal level of the timing signal $P_{out}$ is changed to the high level H, the output voltage $V_h$ of the control unit 9 is measured. Then, the measured output voltage $V_h$ is converted into the resonance frequency $f_e$. Moreover, after the signal level of the timing signal $P_{out}$ is changed to the low level L, the output voltage $V_l$ of the control unit 9 is measured. Then, the difference between the output voltages, namely, $(V_h-V_l)$ is obtained and is further converted into the frequency deviation df. Thus, the frequency shift $\Delta_e$ is obtained. Subsequently, similarly as in the case of the aforementioned embodiment, the dielectric constant $\epsilon$ and the electric constant $\sigma$ are found from such a resonance frequency $f_e$ and the frequency shift $\Delta_e$.

In the case of each of such modifications of this embodiment, the methanol mixing ratio M is calculated on the basis of the output voltage of the control unit 9 instead of measuring the frequency provided from the frequency divider 11. Thus the frequency divider 11, the sample-and-hold circuits 14 and 15 and the subtractor 16, which usually increase the size of the circuit, can be saved. Consequently, such modifications have an advantage in that the configuration of the circuit becomes simple and the manufacturing cost of the circuit is reduced.

EMBODIMENT 3

As described above, in the case of embodiment 2, the phase difference target value is alternately set as the first target value 0° and the second target value $\theta_2$. Further, the resonance frequency and the frequency shift corresponding to a change in the phase difference are obtained by alternately changing these target values by means of the target value switching unit 8. The resonance frequency and the frequency shift corresponding to a change in the phase difference, however, may be obtained by setting only the first target value 0° in the control unit 9 and then by modulating the phase difference target value around the first target value by using an AC signal, the frequency of which is sufficiently lower than the resonance frequency.

Figure 7:
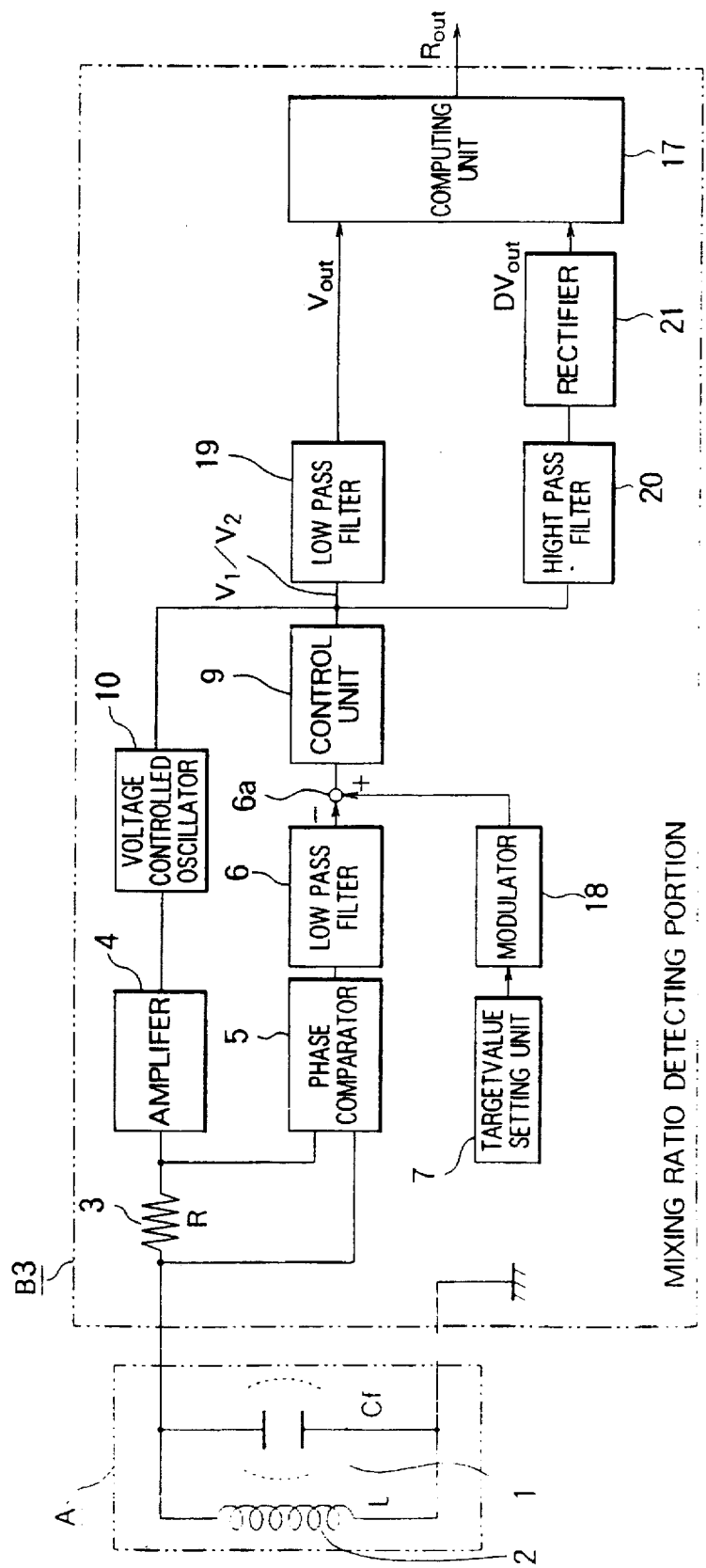
FIG. 7 is a diagram for illustrating the configuration of a third fuel mixing ratio detecting device embodying the present invention, namely, embodiment 3 of the present invention.

Hereinafter, this embodiment, namely, embodiment 3 will be described by referring to the accompanying drawings. FIG. 7 is a diagram illustrating the configuration of a fuel mixing ratio detecting device in accordance with a third embodiment of the present invention, namely, embodiment 3 of the present invention. Incidentally, in this figure, like reference symbols designate like or corresponding parts of FIG. 6. Mixing ratio detecting portion $B_3$ of this embodiment is provided with a modulator 18 for changing the control target phase of the control unit 9 within an amplitude Δθ from the first target value 0°, which is the middle value, by using a frequency $f_v$ sufficiently lower than the resonance frequency $f_0$ of the system (PLL circuit), and is further provided with a low-pass filter 19 for eliminating an AC component due to a modulation signal from the output voltage of the control unit 9 and for outputting a DC voltage corresponding to the resonance frequency $f_0$ to the computing unit 17 as the output voltage $V_{out}$ of the control unit 9, a high-pass filter 20 for removing a DC component from the output voltage of the control unit 9 and for outputting an AC component, namely, a modulation signal, and a rectifier 21 for rectifying the AC component outputted from the high-pass filter 20 and for outputting a resultant voltage to the computing unit 17 as the deviation voltage $DV_{out}$ corresponding to the frequency shift Δf.

Next, an operation of this embodiment will be described hereinbelow. First, the modulator 18 changes the control target phase of the control unit 9 within the amplitude Δθ from the first target value 0°, which is the middle value, by using the frequency $f_v$ sufficiently lower than the resonance frequency $f_0$ of the system. At that time, the output frequency of the voltage-controlled oscillator 10 changes at the frequency $f_v$ and the phase difference between the voltages at both terminals of the resistance 3 similarly changes, so that the phase-difference voltage of the phase comparator 5 changes at the frequency $f_v$.

Figure 8:
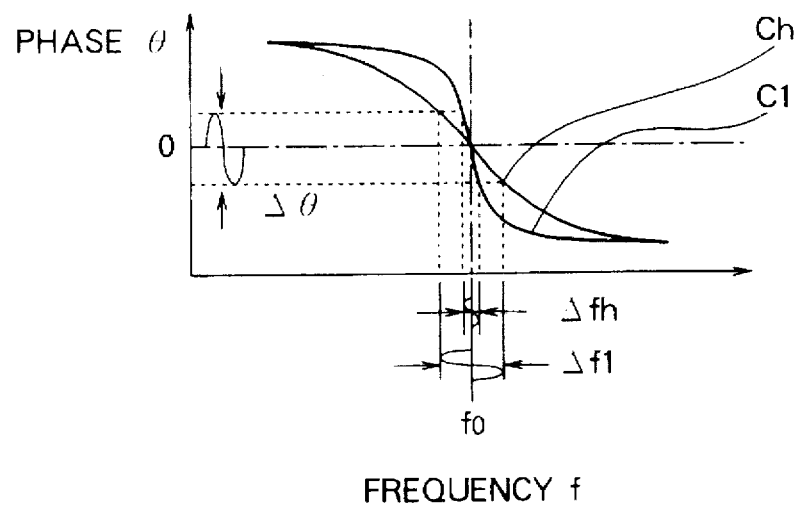
FIG. 8 is a graph for showing the frequency-phase characteristics of a voltage-controlled oscillator of embodiment 3 to describe an operation thereof.

The output of the phase comparator 5 is, however, averaged by the low-pass filter 6. Thus, the output phase of the low-pass filter 6 becomes 0°. Consequently, the output of the voltage-controlled oscillator 10 changes at the modulation frequency $f_v$ around the resonance frequency $f_0$, which is the middle value, with the frequency amplitude Δf corresponding to the phase amplitude Δθ, as shown in FIG. 8 which illustrates the phase characteristics of the system. At that time, in the output voltage of the control unit 9, an AC voltage having the frequency $f_v$ and the amplitude Δf is superimposed on a DC voltage corresponding to the resonance frequency $f_0$, which is the middle value.

Then, the AC component of the output voltage of the control unit 9 is eliminated by the low-pass filter 19. Thus the output $V_{out}$ of the low-pass filter 19 becomes an output voltage ($V_{out}$) corresponding to the resonance frequency $f_0$. Further, the DC component of the output of the control unit 9 is eliminated by the high-pass filter 20. On the other hand, the modulation signal, namely, the AC component is rectified by the rectifier 21 and the rectified signal is outputted therefrom. Thus the signal outputted from the rectifier 2 comes to represent the deviation voltage $DV_{out}$ corresponding to the frequency amplitude Δf. The CPU of the computing unit 17 inputs the output voltage $V_{out}$ of the control unit 9 and the deviation voltage $DV_{out}$ from the analog input port thereof. Further, the CPU computes the dielectric constant by converting the output voltage $V_{out}$ into the resonance frequency $f_e$. Moreover, the CPU also computes the electric conductivity σ by converting the deviation voltage $DV_{out}$ into the frequency deviation $Δf_e$ and thereafter obtaining the frequency shift $Δ_e = Δf_e/f_e$. Furthermore, the methanol mixing ratio M is calculated from the results of such computations by performing a procedure similar to that performed in the case of embodiment 1. Then, a signal representing the calculated mixing ratio is outputted from the output port thereof as an output signal $R_{out}$ thereof.

Alternatively, the methanol mixing ratio M may be computed as the result of the dielectric constant ε and the electric conductivity σ being obtained by using the $V_{out}$-ε map and the $DV_{out}/V_{out}$-σ map which are preliminarily stored in the ROM, without converting the output voltage $V_{out}$ and the deviation voltage $DV_{out}$ into frequencies.

Such a modification of this embodiment has an advantage in that the methanol mixing ratio M can be detected by computing the dielectric constant ε and the electric conductivity σ at the same time on the basis of a single phase difference target value without changing the phase-difference target value with the lapse of time.

EMBODIMENT 4

In the case of the aforementioned embodiment, the methanol mixing ratio M is detected from the control voltage output of the control unit 9. The methanol mixing ratio M, however, can be detected from the frequency output of the voltage-controlled oscillator 10 by performing a method of modulating the phase-difference target value.

In the device having configuration as illustrated in FIG. 7, a low-frequency signal (not shown) having a frequency of f/N (N is the frequency division ratio), which is obtained by dividing the frequency of an output of the voltage-controlled oscillator 10 by means of the frequency divider 11, is inputted to the computing unit 17 through the digital input port thereof. The computing unit 17 measures the period T of the low-frequency signal in a predetermined time. Further, in this predetermined time, the instantaneous frequency f (=N/T) is obtained by performing an inverse operation. Thereafter, the average value of the instantaneous frequency f in the predetermined time is calculated and is further set as the resonance frequency $f_e$. Moreover, the frequency shift $Δ_e$ is obtained from the difference Δf between the maximum value $f_{max}$ and the minimum value $f_{min}$ of the instantaneous frequency in the predetermined time and from the resonance frequency $f_e$. Subsequently, the methanol mixing ratio M is detected as the result of the dielectric constant ε and the electric conductivity σ being obtained from such a resonance frequency $f_e$ and frequency shift $Δ_e$ by performing a method similar to the method employed in embodiment 3.

This embodiment has advantages similar to those of embodiment 3. Moreover, this embodiment has additional advantages in that a circuit error of the (PLL) system can be eliminated because the resonance frequency of the LC parallel resonance circuit is directly detected and that the methanol mixing ratio M can be detected more accurately.

EMBODIMENT 5

Figure 9:
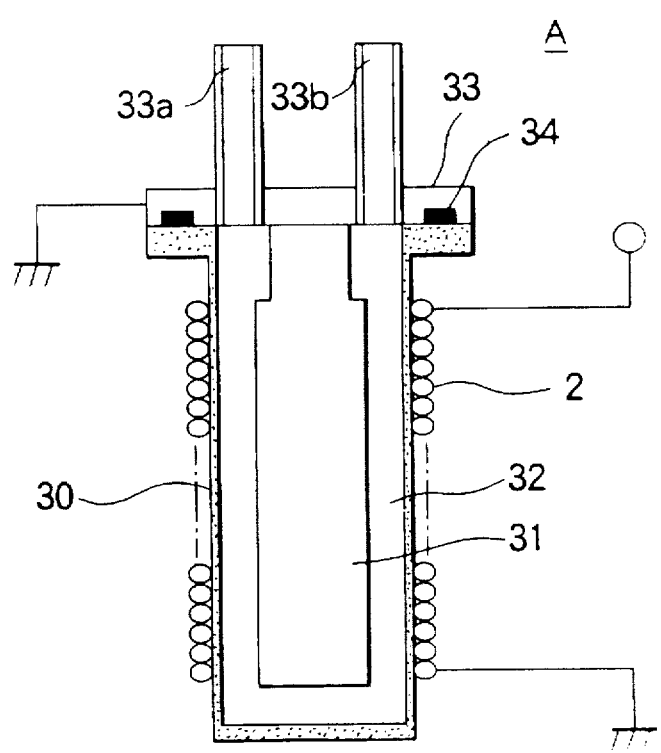
FIG. 9 is a sectional diagram of a sensor portion A of embodiment 5 of the present invention.
Figure 10:
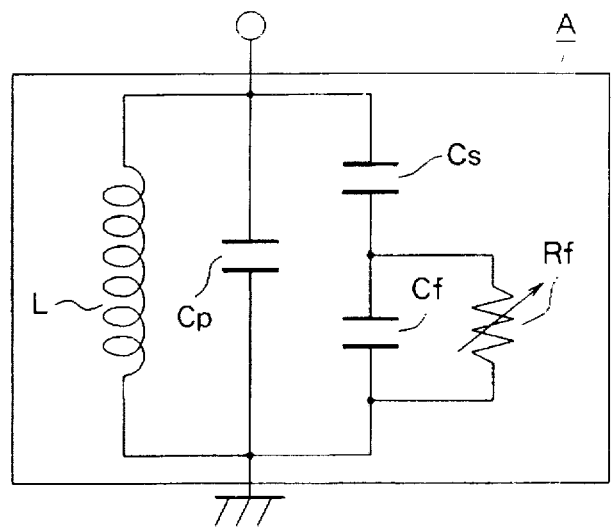
FIG. 10 is a circuit diagram for showing the configuration of an equivalent circuit of the sensor portion A.
Figure 11:
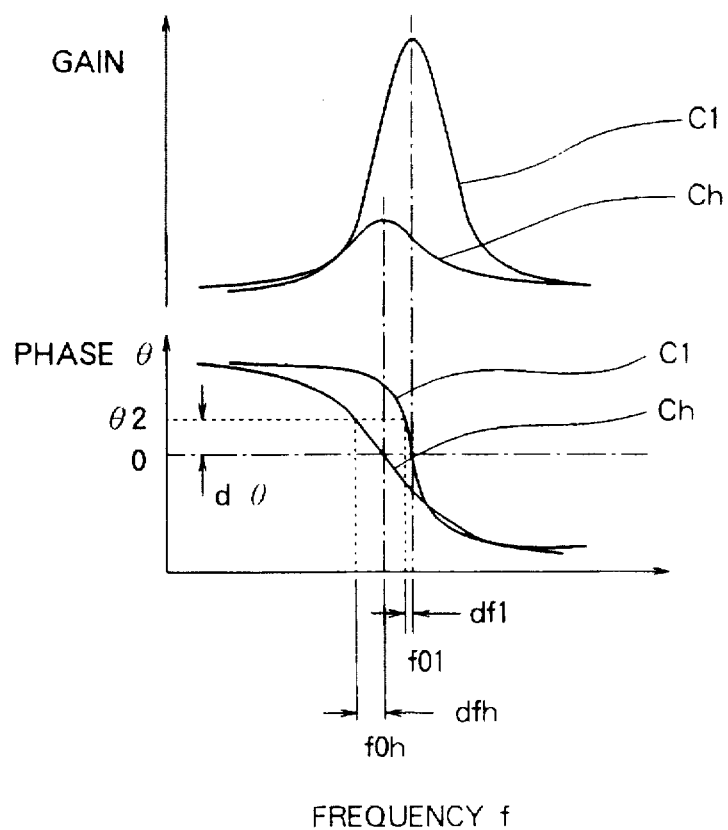
FIG. 11 is a graph for illustrating the frequency characteristics of an LCR series-parallel circuit of FIG. 10.
Figure 12:
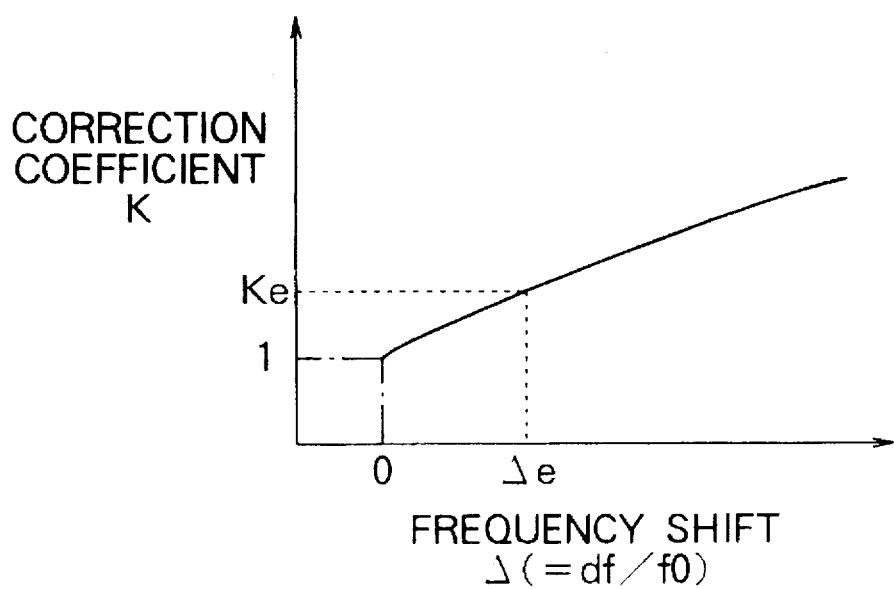
FIG. 12 is a graph for showing the relation between the frequency shift $\Delta$ and the correction coefficient k for the resonance frequency $f_0$, which is employed in embodiment 5 of the present invention.
Figure 19:
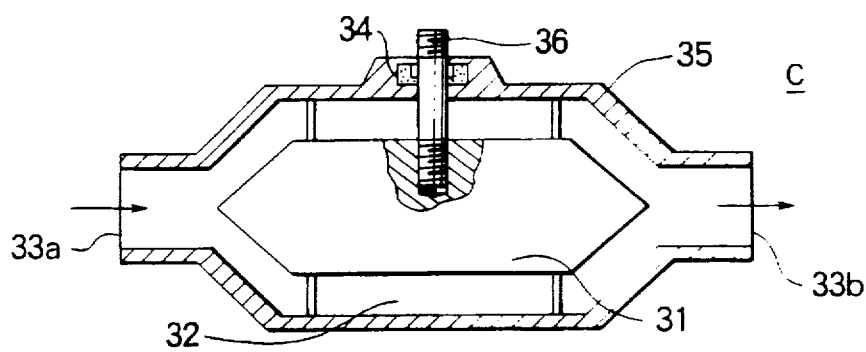
FIG. 19 is a sectional diagram of the electrostatic capacity detecting portion C of the conventional device.

FIGS. 9 to 12 are diagrams illustrating an embodiment whose configuration is obtained by replacing each of the sensor portions A of embodiments 1 to 3 with another sensor portion having an electrostatic capacity detecting portion of the structure different from that of the conventional electrostatic capacity detecting portion of FIG. 19. FIG. 9 is a sectional view of the sensor portion A of embodiment 5. FIG. 10 is a circuit diagram showing the configuration of an equivalent circuit of this sensor portion A. FIG. 11 is a graph illustrating the frequency characteristics of an LCR series-parallel circuit in which a resistance R is connected in series to the sensor portion A of FIG. 9. FIG. 12 is a graph showing the relation between the frequency shift Δ and the correction coefficient k for the resonance frequency $f_0$, which is employed in embodiment 5 of the present invention. The sensor portion A of FIG. 9 has a cylindrical housing 30 made of an insulating material, on the circumferential wall of which a single-layer winding coil 2 is provided. Further, a cylindrical internal electrode 31 is provided in the cylindrical housing 30 with a predetermined space or gap (namely, a fuel passage to be described later) formed between the electrode 31 and the internal wall of the cylindrical housing

30.

Further, the fuel passage 32 is formed between the cylindrical housing 30 and the internal electrode 31. A flange 33 is electrically connected to the internal electrode 31. Fuel ports 33a and 33b are fitted into the flange. A ring-like fuel seal 34 is mounted on the bottom surface of the flange, which is in contact with the top surface of the cylindrical housing 30. Incidentally, a part, which is brought into contact with liquid or fuel, of each composing element of the sensor portion A is made of a material which has a high fuel-resistance. An end of the coil 2 of this figure is connected in series to the resistance of FIG. 3. Further, as illustrated in this figure, the other end of the coil 2 and the internal electrode 31 are grounded.

In the sensor portion A of FIG. 9, the inner cylindrical surface of the coil 2 serves as an electrode. Further, the portion for detecting the electrostatic capacity $C_f$ of fuel filling up the fuel passage 32 is constituted by the part or gap sandwiched between the internal electrode 31 and the inner wall surface of the cylindrical housing 30. Practically, the equivalent circuit of such a sensor portion A is an LCR distributed constant circuit. A circuit simplified as illustrated in FIG. 10, however, can be substituted for by such a practical equivalent circuit.

In FIG. 10, reference character $C_s$ designates the capacity of the cylindrical wall of the housing 30. As shown in this figure, the capacitor having the electrostatic capacity $C_f$ of fuel is connected in series to the capacitor having the capacity $C_s$. Further, the coil 2 having the reactance L is connected in parallel to these capacitors connected in series with each other. In the case of such a sensor portion A, the resistance appearing between both terminals of the capacitor having the capacity $C_s$, namely, the resistance of the cylindrical wall of the housing 30, is high. Therefore, even when the electric conductivity σ of the fuel increases and the resistance $R_f$ becomes small, a reduction in Q-factor is small. The resonance frequency $f_0$ of the sensor portion A is, however, not expressed by the simple equation (1). As illustrated in FIG. 11, the frequency characteristics are such that the higher the electric conductivity σ rises, the lower the resonance frequency $f_0$ becomes.

Thus, the CPU of the computing unit 12 computes the electric conductivity $σ_e$ corresponding to the measured frequency shift $Δ_e$ therefrom by using the Δ-σ map (see FIG. 4). Moreover, the CPU reads the correction coefficient $k_e$ corresponding to $Δ_e$ from data representing the relation between the correction coefficient k and the frequency shift Δ, which is preliminarily stored in the ROM, as illustrated in the graph of FIG. 12. Such a correction coefficient k is preliminarily stored in the ROM by analyzing a change in resonance frequency $f_0$, which is caused by the variation in electric conductivity σ when the dielectric constant ε is invariable. The CPU corrects the change in resonance frequency $f_e$, which is caused owing to the change in electric conductivity σ, by using the correction coefficient $k_e$. Then, the CPU computes the dielectric constant $ε_e$ corresponding to the resonance frequency $k_e f_e$ from the corrected resonance frequency $k_e f_0$ by using the $f_0$-ε map. Finally, the CPU calculates the methanol mixing ratio M from the computed dielectric constant $ε_e$ and the computed electric conductivity $σ_e$.

This embodiment has an advantage in that even in the case of using the sensor portion in which the resonance frequency $f_0$ varies according to the electric conductivity $σ_e$, the methanol mixing ratio M can be computed accurately by correcting the resonance frequency $f_0$ in accordance with a change in the electric conductivity $σ_e$. This embodiment can be implemented on the basis of the resonance frequency $f_0$ inputted or computed in and the electric conductivity σ computed in the computing units 12 and 17 of the mixing ratio detecting portions or units $B_1$, $B_2$ and $B_3$.

EMBODIMENT 6

In the case of each of the aforementioned embodiments, the electric conductivity σ is computed by causing a deviation of the target value of the phase difference so as to give rise to a frequency shift. The electric conductivity σ, however, can be computed from the impedance of the LC parallel resonance circuit at the time of resonating without causing a deviation of the target value of the phase difference. This is because the impedance of the LC parallel resonance circuit at the time of resonating becomes equal to the resistance $R_f$ determined by the electric conductivity σ of the fuel. The electric conductivity σ, which is proportional to the reciprocal of the impedance of the LC parallel resonance circuit, can be obtained by detecting the impedance of the resonance circuit at the time of resonating.

Figure 13:
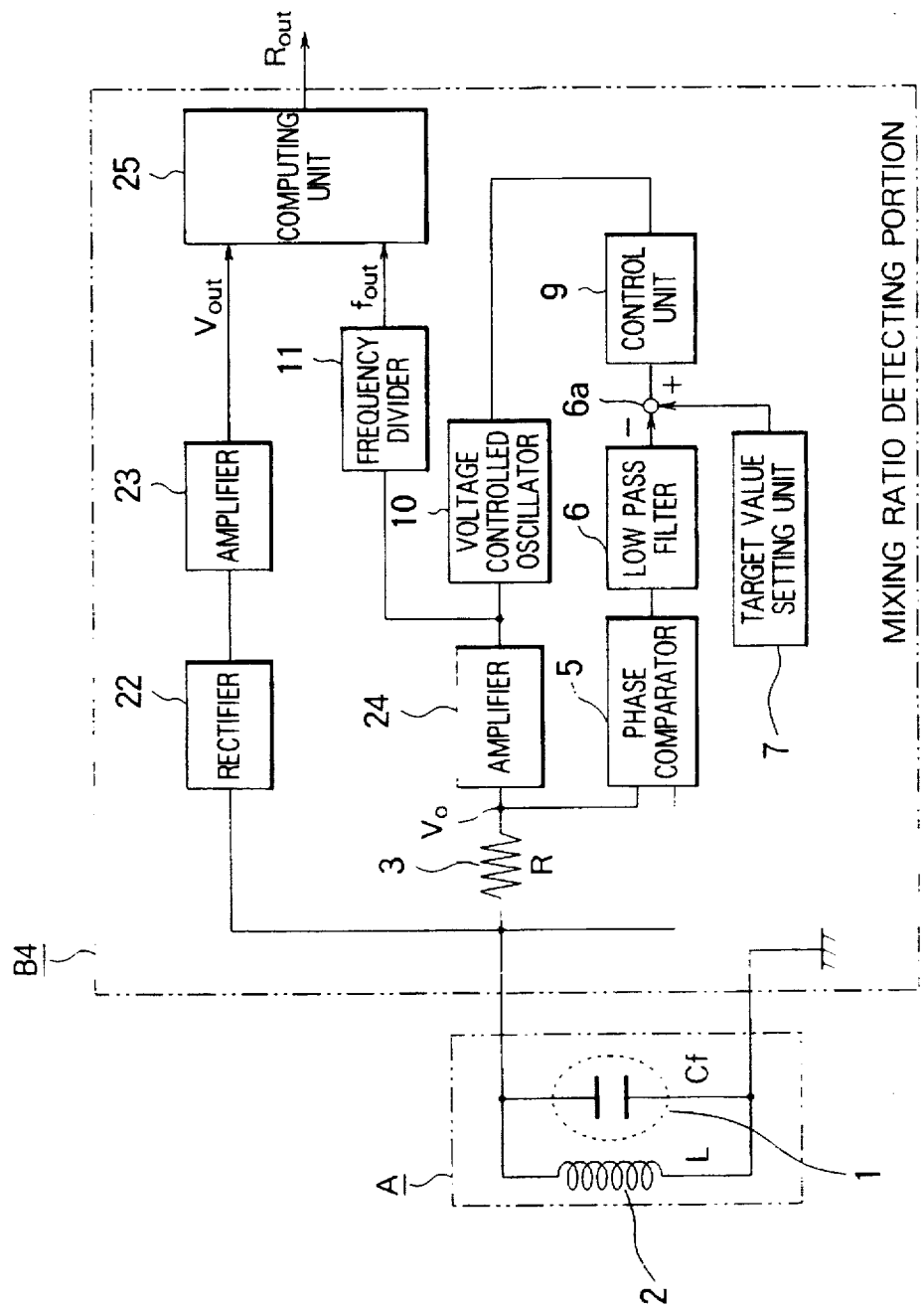
FIG. 13 is a diagram for illustrating the configuration of a sixth fuel mixing ratio detecting device embodying the present invention, namely, embodiment 6 of the present invention.

Hereinafter, this embodiment, namely, embodiment 6, will be described by referring to the accompanying drawings. FIG. 13 is a diagram illustrating the configuration of a fuel mixing ratio detecting device in accordance with a sixth embodiment of the present invention, namely, embodiment 6 of the present invention. Incidentally, in this figure, like reference symbols designate like or corresponding parts of FIG. 1. Mixing ratio detecting portion $B_4$ of this embodiment is provided with a rectifier 22 for detecting and rectifying an output voltage $V_1$ in the LC parallel resonance circuit from the connection part between the resistance 3 and the sensor portion A and for outputting a rectified signal, an amplifier 23 for amplifying an output signal of the rectifier 22 at a predetermined amplification factor $g_1$, a constant voltage amplifier 24 for applying a constant voltage output $V_0$, which is obtained by amplifying an oscillation output of the voltage-controlled oscillator 10 to a constant voltage level, to the series circuit comprising the resistance R and the LC parallel resonance circuit, and a computing unit 25 for computing the electric conductivity σ from the output voltage $V_1$, the constant voltage output $V_0$, the value R of the resistance 3, the amplification factor $g_1$ of the amplifier 23 and the constant k determined by the shape of the sensor A, for computing the dielectric constant ε of the fuel from the resonance frequency $f_{out}$ of a signal outputted by the frequency divider 11 after a frequency division is accomplished, and for computing a methanol mixing ratio of the fuel from results of the computations.

Next, an operation of this embodiment will be described hereinbelow. First, a high-frequency signal (namely, a constant voltage output $V_0$) amplified by the constant voltage amplifier 24 is applied to the series circuit comprising the resistance 3 and the sensor portion A. At that time, the frequency of the applied high-frequency signal is controlled through the PLL in such a manner that the phase difference between the voltages at both terminals of the resistance 3 becomes equal to the target value 0°. Thus, in the case where the phase difference between these voltages becomes equal to the target value 0°, the frequency of the high-frequency signal matches the resonance frequency $f_0$ of the LC parallel resonance circuit.

The resonance frequency $f_0$ of the high-frequency signal is divided by N by the frequency divider 11. Thus, a resultant signal having a frequency $f_{out}=f_0/N$ is inputted to the digital input port (not shown) of the computing unit 25. On the other hand, the output voltage $V_1$ appearing at the connection portion between the sensor portion A and the resistance 3 is rectified by the rectifier 22. Then, the rectified signal is inputted to and is further amplified by the amplifier 23. The amplified signal is inputted to the analog port of the computing unit 25 as $V_{out}$. At that time, the impedance Z of the sensor portion A is equivalent to the pure resistance $R_f$, namely, the electric conductivity σ. The electric conductivity σ is given by the following equation by using the output voltage $V_1$, the constant voltage output $V_0$, the value R of the resistance 3, the amplification factor $g_1$ of the amplifier 23 and the constant k determined by the shape of the sensor A:

$$\sigma = 1/kR*(g_1 V_0/V_{out} - 1) \quad (6)$$

Figure 16A:
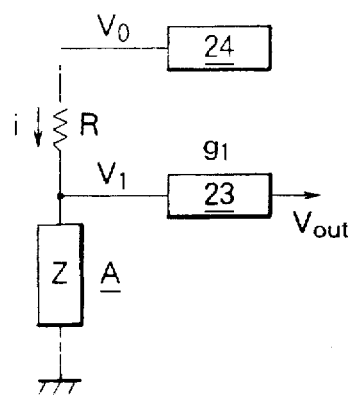
FIG. 16(a) is a diagram for showing the configuration of an equivalent circuit of a portion including an LC parallel circuit and the surrounding circuits in embodiment 6 to illustrate an operation of embodiment 6 of the present invention.

Next, how equation (6) is introduced will be described hereinbelow by using the equivalent circuit of FIG. 16(a).

Here, it is to be noted that a voltage developed across both terminals of the resistor 3 having the resistance R is expressed as the following equation (6a).

$$V_0 - V_1 = Ri \quad (6a)$$

Further, the voltage (the output voltage $V_1$) developed across both terminals of the LC parallel resonance circuit is expressed as the following equation (6b):

$$V_1 = Zi \quad (6b)$$

where Z designates the impedance of the LC parallel resonance circuit.

Next, in order to obtain an admittance (1/Z) of the LC parallel resonance circuit at the time of resonating, the following equation (6c) is derived from equations (6a) and (6b).

$$R/Z = V_0/V_1 - 1 \quad (6c)$$

Furthermore, the admittance at the time of resonating is expressed as follows:

$$1/Z = 1/R_f = k\sigma \quad (6d)$$

Additionally, the voltage $V_1$ is expressed by the following equation (6e) using the output voltage $V_{out}$ of the amplifier 23.

$$V_1 = V_{out}/g_1 \quad (6e)$$

Thus, the electric conductivity σ is expressed as the following equation (6f) obtained from the equations (6c) and (6d).

$$Rk\sigma = V_0/V_1 - 1 \quad (6f)$$

Consequently, the electric conductivity σ is obtained as follows:

$$\sigma = 1/kR(V_0/V_1 - 1) \quad (6g)$$

Incidentally, the electric conductivity σ is finally expressed as equation (6) by expressing the voltage $V_1$ as equation (6e) and replacing $V_1$ in equation (6g) with $V_{out}/g_1$.

The CPU of the computing unit 25 computes the dielectric constant $\epsilon_e$ corresponding to the resonance frequency $f_e$, as illustrated in FIG. 3, from the frequency $f_e$ calculated from $f_{out}$ read from the digital input port thereof by using the $f_0$-$\epsilon$ map. Further, the CPU calculates the methanol mixing ratio M from the computed dielectric constant $\epsilon_e$ and the electric conductivity $\sigma_e$ which is calculated in the computing unit 25 by using the equation (6).

As is apparent from the foregoing description, in the case of this embodiment, the electric conductivity σ is computed by detecting the impedance of the LC parallel resonance circuit. Thus, this embodiment has an advantage in that the configuration of the mixing ratio detecting circuit can be simplified in comparison with the case in which the electric conductivity is computed by changing the phase-difference target value of the PLL.

EMBODIMENT 7

In the case of the aforementioned embodiment 6, a constant-voltage amplification is performed by the constant-voltage amplifier 24 on a high-frequency signal outputted from the voltage-controlled oscillator 10. Then, the amplified signal is outputted therefrom to the LC parallel resonance circuit. An ordinary amplifier, however, may be used instead of the constant-voltage amplifier 24.

Figure 14:
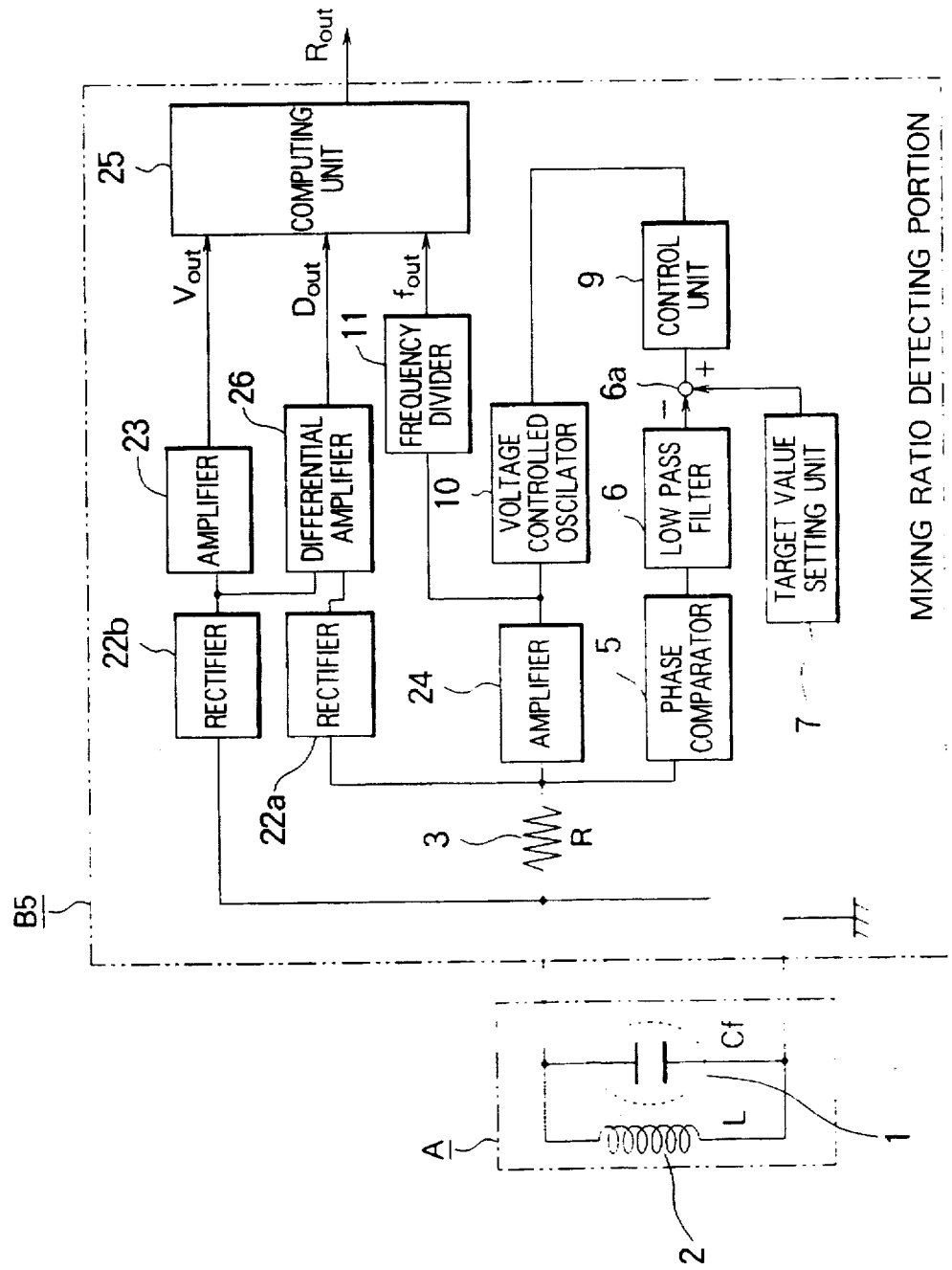
FIG. 14 is a diagram for illustrating the configuration of a seventh fuel mixing ratio detecting device embodying the present invention, namely, embodiment 7 of the present invention.

Hereinafter, this embodiment, namely, embodiment 7, will be described by referring to the accompanying drawings. FIG. 14 is a diagram illustrating the configuration of a fuel mixing ratio detecting device in accordance with a seventh embodiment of the present invention, namely, embodiment 7 of the present invention. Incidentally, in this figure, like reference symbols designate like or corresponding parts of FIG. 13. Mixing ratio detecting portion $B_5$ of this embodiment is provided with an amplifier 4 for applying an output voltage $V_0$ obtained by amplifying a high-frequency signal outputted from the voltage-controlled oscillator 10 to a series circuit comprising a resistance 3 and an LC parallel resonance circuit, a rectifier 22a for rectifying an output voltage $V_0$ of the amplifier 4, a rectifier 22b for rectifying a voltage $V_1$ developed across the LC parallel resonance circuit, an amplifier 23 for amplifying an output signal of the rectifier 22b and for outputting the amplified signal as an output voltage $V_0$, and a differential amplifier 26 for amplifying a deviation between outputs of the rectifiers 22a and 22b and for outputting the deviation to a computing unit 25 as a deviation voltage $DV_{out}$.

Next, an operation of this embodiment will be described hereinbelow. First, a signal having the resonance frequency $f_e$ is inputted from the frequency divider 11 to the computing unit 25 as $f_{out}$. Moreover, a voltage developed across the LC parallel resonance circuit at the time of resonating is inputted to the computing unit 25 through the rectifier 22a and the amplifier 23 as an output voltage $V_{out}$.

Furthermore, the deviation between an output of the rectifier 22b and the rectified output of the amplifier 4 is inputted to the computing unit 25 as the deviation voltage $DV_{out}$. The deviation voltage $DV_{out}$ corresponds to an electric current flowing through the LC parallel resonance circuit.

The computing unit 25 obtains the electric conductivity σ corresponding to the impedance of the sensor portion (the LC parallel resonance circuit) at the time of resonating by using the following equation (7) from the output voltage $V_{out}$, the deviation voltage $DV_{out}$, the preliminarily set amplification factor $g_2$ of the amplifier 23, the amplification factor $g_3$ of the differential amplifier 26, the value R of the resistance 3 and the constant k determined by the shape of the sensor A:

$$\sigma = 1/kR * g_2 DV_{out}/(g_3 V_{out}) \quad (7)$$

Figure 16B:
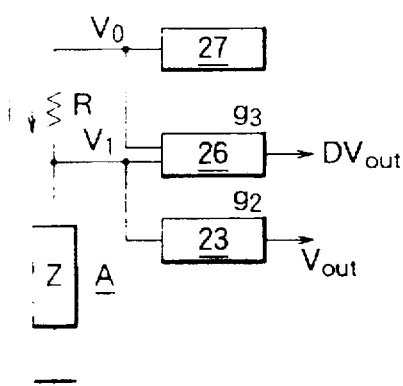
FIG. 16(b) is a diagram for showing the configuration of an equivalent circuit of a portion including an LC parallel circuit and the surrounding circuits in embodiment 7 to illustrate an operation of embodiment 7 of the present invention.

Next, how equation (7) is introduced will be described hereinbelow by using the equivalent circuit of FIG. 16(b).

Here, it is to be noted that a voltage developed across both terminals of the resistor 3 having the resistance R is expressed as the following equation (7a).

$$V_0 - V_1 = Ri \tag{7a}$$

Further, the voltage (the output voltage $V_1$) developed across both terminals of the LC parallel resonance circuit is expressed as the following equation (7b):

$$V_1 = Zi \tag{7b}$$

where Z designates the impedance of the LC parallel resonance circuit.

Next, in order to obtain an admittance (1/Z) of the LC parallel resonance circuit at the time of resonating, the following equation (7c) is derived from the equations (7a) and (7b).

$$R/Z = (V_0 - V_1)/V_1 \tag{7c}$$

Furthermore, the admittance at the time of resonating is expressed as follows:

$$1/Z = 1/Rf = k\sigma \tag{7d}$$

Additionally, the voltage $V_1$ is expressed as the following equation (7e) by using the output voltage $V_{out}$ of the amplifier 23.

$$V_1 = V_{out}/g_2 \tag{7e}$$

Further, the voltage $(V_0 - V_1)$ developed across the resistance 3 (R) is expressed by the following equation using the differential voltage $DV_{out}$ of the differential amplifier 26.

$$V_0 - V_1 = DV_{out}/g_3 \tag{7f}$$

Thus, the electric conductivity $\sigma$ is expressed as the following equation (7g) obtained from the equations (7c) and (7d).

$$Rk\sigma = (V_0 - V_1)/V_1 \tag{7g}$$

Consequently, the electric conductivity $\sigma$ is obtained as follows:

$$\sigma = 1/kR(V_0 - V_1)/V_1 \tag{7h}$$

Incidentally, the electric conductivity $\sigma$ is finally expressed as equation (7) by expressing the voltage $V_1$ as equation (7e), expressing the voltage $(V_0 - V_1)$ as equation (7f) and replacing $(V_0 - V_1)$ and $V_1$ in equation (7h) with equations (7e) and (7f), respectively.

The CPU of the computing unit 25 computes the dielectric constant $\epsilon_e$ corresponding to the resonance frequency $f_e$, as illustrated in FIG. 3, from the frequency $f_e$ calculated from $f_{out}$ read from the digital input port thereof by using the equation (4) or the $f_0$-$\epsilon$ map. Further, the CPU calculates the methanol mixing ratio M from the computed dielectric constant $\epsilon_e$ and the electric conductivity $\sigma_e$ which is calculated in the computing unit 25 by using equation (7).

As is apparent from the foregoing description, in the case of this embodiment, the electric conductivity $\sigma$ is computed by detecting the impedance of the LC parallel resonance circuit. Thus, this embodiment has an advantage in that the configuration of the mixing ratio detecting circuit can be simplified in comparison with the case in which the electric conductivity is computed by changing the phase-difference target value of the PLL.

EMBODIMENT 8

In the case of the aforementioned embodiment 7, the electric conductivity $\sigma$ is computed merely on the basis of the impedance of the LC parallel resonance circuit. The amplification factor of the amplifier 4, however, may be changed according to the electric conductivity $\sigma$ which corresponds to the impedance of the sensor portion A, namely, the LC parallel resonance circuit at the time of resonating.

Figure 15:
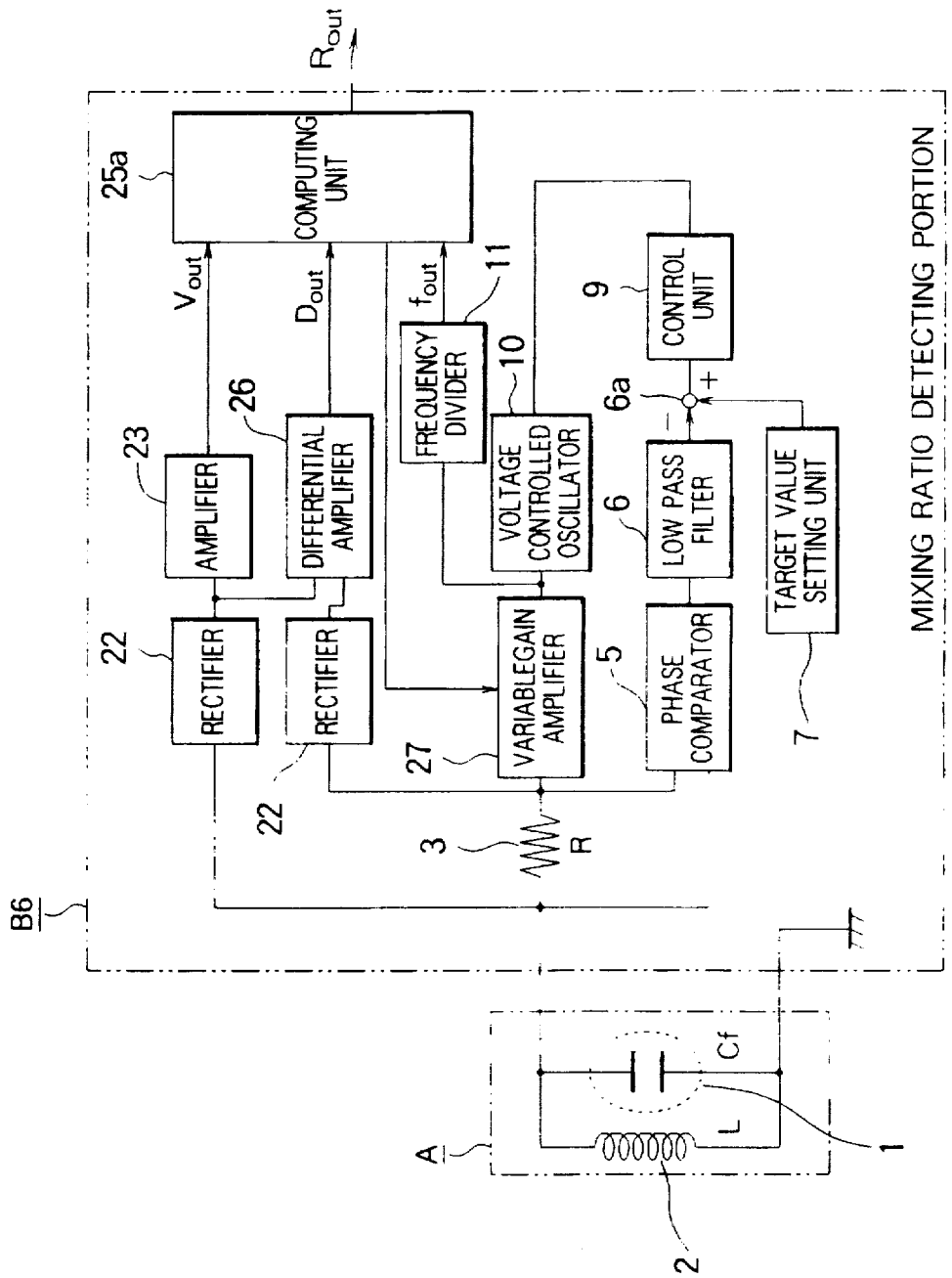
FIG. 15 is a diagram for illustrating the configuration of an eighth fuel mixing ratio detecting device embodying the present invention, namely, embodiment 8 of the present invention.

Hereinafter, this embodiment, namely, embodiment 8, will be described by referring to the accompanying drawings. FIG. 15 is a diagram illustrating the configuration of a fuel mixing ratio detecting device in accordance with an eighth embodiment of the present invention, namely, embodiment 8 of the present invention. Incidentally, in this figure, like reference symbols designate like or corresponding parts of FIG. 14. Mixing ratio detecting portion $B_6$ of this embodiment is provided with a computing unit 25a having a function of changing the amplification factor of a high-frequency signal outputted from the voltage-controlled oscillator 10 according to the value of the computed electric conductivity $\sigma$ in addition to the functions of the computing unit 25 of embodiment 6 and with a variable gain amplifier 27 whose amplification factor is variable according to a control signal outputted from the computing unit 25a.

Next, an operation of this embodiment, namely, embodiment 8, will be described hereinbelow. In the case where the electric conductivity $\sigma$, which is computed when the LC parallel resonance circuit resonates, is small, namely, in the case where the impedance of the LC parallel resonance circuit is large, the voltage $V_1$ developed across the LC parallel resonance circuit becomes high. Consequently, there is the possibility that the difference between the levels of the voltages at both terminals of the resistance 3 becomes small and the differential voltage $DV_{out}$ outputted from the differential amplifier 26 also becomes small and thus the precision of calculation of the electric conductivity $\sigma$ is deteriorated. In contrast, in the case where the impedance is small, the voltage $V_1$ becomes low. Therefore, there is the possibility that the precision of a phase comparison performed in the phase comparator 5 is degraded.

Thus, in the case where the computed electric conductivity $\sigma$, namely, the impedance of the LC parallel resonance circuit, is not less than a predetermined value, the computing unit 25a controls the variable gain amplifier 27 in such a manner that the amplification factor thereof becomes large and as a result, the difference between the levels of the voltages at both terminals of the resistance 3 becomes large and consequently, the differential amplifier 26 can secure an appropriate differential voltage $DV_{out}$. Similarly, in the case where the impedance of the LC parallel resonance circuit is not more than the predetermined value, the computing unit 25a controls the variable gain amplifier 27 in such a fashion that the amplification factor thereof becomes large and as a result, the level of the voltage $V_1$ becomes high. Thus, the device secures the high precision of a phase comparison in such a manner that the voltage amplitude becomes sufficiently larger than the hysteresis width of a threshold level.

Consequently, the methanol mixing ratio M can be obtained accurately irrespective of a change in electric conductivity $\sigma$ by changing the level of a high-frequency signal according to the impedance of the LC parallel resonance circuit.

In the cases of the aforementioned embodiments 6, 7 and 8, the resonance frequency $f_0$ is detected by using the frequency divider 11. A voltage output of the voltage-controlled oscillator, however, may be used for detecting the resonance frequency $f_0$. In this case, a computing unit 17 having only analog input ports may be employed.

EMBODIMENT 9

In the case of each of the aforementioned embodiments 6, 7 and 8, the sensor portion A is of the type that even when the electric conductivity σ changes, only the gain of the LC parallel resonance circuit varies but the resonance frequency thereof is constant or invariant. In the case of embodiment 9, a sensor portion, which is of the type that the resonance frequency thereof changes when the electric conductivity σ varies similarly as the sensor portion of FIG. 9, is used in the fuel mixing ratio detecting device which has the configuration as illustrated in FIGS. 13 and 14 and employs a method of correcting the resonance frequency $f_{out}$ ($f_e$) inputted from a frequency divider. Such a method will be described hereinbelow.

Figure 17:
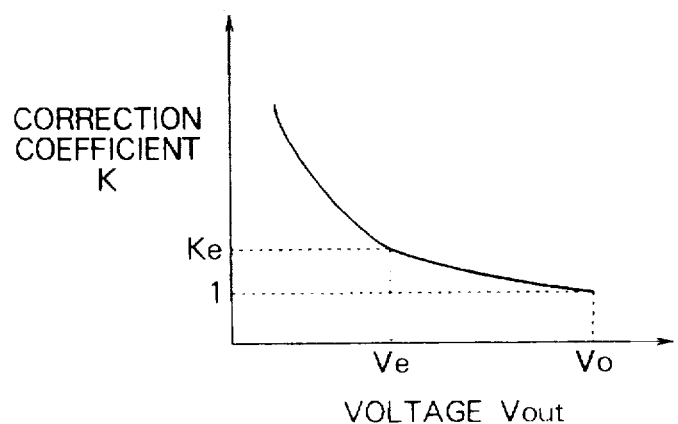
FIG. 17 is a graph for illustrating the relation between the output voltage $V_{out}$ of FIG. 13 and the correction coefficient k for the resonance frequency $f_0$.

FIG. 17 is a graph illustrating the relation between the output voltage $V_{out}$ outputted from the amplifier 23 of FIG. 13 and the correction coefficient k for the resonance frequency. The computing unit 25 reads the correction coefficient $k_e$, which corresponds to the output voltage $V_{out}$ at the time of resonating, from a k-$V_{out}$ map which is preliminarily generated according to this graph and stored in the ROM. Then, the computing unit 25 corrects a change in the resonance frequency $f_e$, which is caused by a variation in the electric conductivity σ, by using the correction coefficient $k_e$. Subsequently, the computing unit 25 computes the dielectric constant $\epsilon_e$ corresponding to the corrected frequency $k_e f_e$ therefrom by using the $f_0$-ϵ map. Finally, the CPU calculates the methanol mixing ratio M from the computed dielectric constant $\epsilon_e$ and the computed electric conductivity $\sigma_e$.

Figure 18:
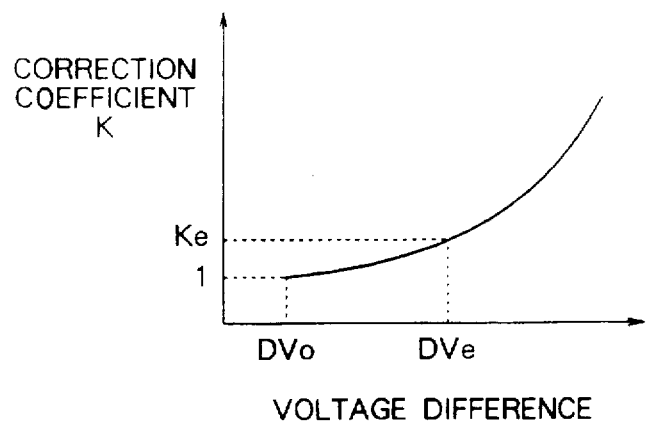
FIG. 18 is a graph for illustrating the relation between the output voltage $DV_{out}$ of FIG. 14 and the correction coefficient k for the resonance frequency $f_0$.

FIG. 18 is a graph illustrating the relation between the output voltage $DV_{out}$ outputted from the differential amplifier 26 of FIG. 14 and the correction coefficient k for the resonance frequency $f_0$. The computing unit 25 reads the correction coefficient $k_e$, which corresponds to the deviation voltage $DV_{out}$ at the time of resonating, from a k-$DV_{out}$ map which is preliminarily generated according to this graph and stored in the ROM. Then, the computing unit 25 corrects a change in the resonance frequency $f_e$, which is caused by a variation in the electric conductivity σ, by using the correction coefficient $k_e$. Subsequently, the computing unit 25 computes the dielectric constant $\epsilon_e$ corresponding to the corrected frequency $k_e f_e$ therefrom by using the $f_0$-ϵ map. Finally, the CPU calculates the methanol mixing ratio M from the computed dielectric constant $\epsilon_e$ and the computed electric conductivity $\sigma_e$.

Such an embodiment has an advantage in that the methanol mixing ratio M can be calculated accurately even when a sensor portion, which is of the type that the resonance frequency $f_0$ changes according to the electric conductivity σ.

Incidentally, in the case of each of the aforesaid embodiments, the CPU is built into the computing unit. The computing unit, however, may be constituted by a circuit which does not use a CPU. Additionally, in the case of each of the aforementioned embodiments, the present invention is applied to the detection of a methanol mixing ratio of methanol blended gasoline. The present invention, however, can be widely applied to detections of mixing ratios of ingredients to a mixed liquid, whose dielectric constant and electric conductivity are changed by mixing ingredients of various kinds.

Although the preferred embodiments of the present invention have been described above, it should be understood that the present invention is not limited thereto and that other modifications will be apparent to those skilled in the art without departing from the spirit of the invention.

The scope of the present invention, therefore, is to be determined solely by the appended claims.

What is claimed is:

1. A fuel mixing ratio detecting device comprising:

an LC resonance circuit having an electrostatic capacity detecting portion for detecting an electrostatic capacity of fuel and means electrically equivalent to a coil connected in parallel with the electrostatic capacity detecting portion;

a phase lock circuit having a voltage-controlled oscillator for generating a high-frequency signal having a frequency determined by a control voltage and for applying the generated high-frequency signal to the LC resonance circuit, a phase comparator for detecting a phase difference between a voltage and a current of the high-frequency signal applied to the LC resonance circuit, and a control unit for controlling the control voltage supplied to the voltage-controlled oscillator according to a difference between the phase difference detected by the phase comparator and a preliminarily set phase-difference target value;

target value switching means for changing the phase difference target value between a first target value and a second target value different from the first target value to thereby set the changed target value in the control unit;

dielectric-constant computing means for computing a dielectric constant of the fuel on the basis of a first control output of the phase lock circuit after the phase-difference target value is changed to the first target value by the target value switching means;

electric-conductivity computing means for computing an electric conductivity of the fuel on the basis of an amount of shift between the first control output, which is outputted from the phase lock circuit after the phase-difference target value is changed to the first target value by the target value switching means, and a second control output, which is outputted from the phase lock circuit after the phase-difference target value is changed to the second target value by the target value switching means; and mixing-ratio detecting means for detecting a fuel mixing ratio of the fuel from the computed dielectric constant and the computed electric conductivity.

2. A fuel mixing ratio detecting device comprising:

an LC resonance circuit having an electrostatic capacity detecting portion for detecting an electrostatic capacity of fuel and means electrically equivalent to a coil connected in parallel with the electrostatic capacity detecting portion;

a phase lock circuit having a voltage-controlled oscillator for generating a high-frequency signal having a frequency determined by a control voltage and for applying the generated high-frequency signal to the LC resonance circuit, a phase comparator for detecting a phase difference between a voltage and a current of the high-frequency signal applied to the LC resonance circuit, and a control unit for controlling the control voltage supplied to the voltage-controlled oscillator according to a difference between the phase difference detected by the phase comparator and a preliminarily set phase-difference target value;

target value switching means for changing a phase difference target value between a first target value and a second target value different from the first target value and for setting the changed target value in the control unit;

dielectric-constant computing means for computing a dielectric constant of the fuel on the basis of the frequency of a first high-frequency signal generated by the voltage-controlled oscillator after the phase-difference target value is changed to the first target value by this target value switching means;

electric-conductivity computing means for computing an electric conductivity of the fuel on the basis of an amount of frequency shift between a frequency of the first high-frequency signal, which is generated by the voltage-controlled oscillator after the phase-difference target value is changed to the first target value by the target value switching means, and a frequency of a second high-frequency signal, which is generated by the voltage-controlled oscillator after the phase-difference target value is changed to the second target value by the target value switching means; and mixing-ratio detecting means for detecting a fuel mixing ratio of the fuel from the computed dielectric constant and the computed electric conductivity.

3. A fuel mixing ratio detecting device comprising:

an LC resonance circuit having an electrostatic capacity detecting portion for detecting an electrostatic capacity of fuel and means electrically equivalent to a coil connected in parallel with the electrostatic capacity detecting portion;

a phase lock circuit having a voltage-controlled oscillator for generating a high-frequency signal having a frequency determined by a control voltage and for applying the generated high-frequency signal to the LC resonance circuit, a phase comparator for detecting a phase difference between a voltage and a current of the high-frequency signal applied to the LC resonance circuit, and a control unit for controlling the control voltage supplied to the voltage-controlled oscillator according to a difference between the phase difference detected by the phase comparator and a preliminarily set phase-difference target value;

target value switching means for changing a phase difference target value between a first target value and a second target value different from the first target value and for setting the changed target value in the control unit;

dielectric-constant computing means for computing a dielectric constant of the fuel on the basis of a first control voltage applied by the control unit to the voltage-controlled oscillator after the phase-difference target value is changed to the first target value by this target value switching means;

electric-conductivity computing means for computing an electric conductivity of the fuel on the basis of an amount of shift between the first control voltage, which is applied by the control voltage to the voltage-controlled oscillator after the phase-difference target value is changed to the first target value by this target value switching means, and a second control voltage, which is applied by the control unit to the voltage-controlled oscillator after the phase-difference target value is changed to the second target value by the target value switching means; and mixing-ratio detecting means for detecting a fuel mixing ratio of the fuel from the computed dielectric constant and the computed electric conductivity.

4. A fuel mixing ratio detecting device comprising:

an LC resonance circuit having an electrostatic capacity detecting portion for detecting an electrostatic capacity of fuel and means electrically equivalent to a coil connected in parallel with the electrostatic capacity detecting portion;

a phase lock circuit having a voltage-controlled oscillator for generating a high-frequency signal having a frequency determined by a control voltage and for applying the generated high-frequency signal to the LC resonance circuit, a phase comparator for detecting a phase difference between a voltage and a current of the high-frequency signal applied to the LC resonance circuit, and a control unit for controlling the control voltage supplied to the voltage-controlled oscillator according to a difference between the phase difference detected by the phase comparator and a preliminarily set phase-difference target value;

target value setting means for setting a first target value in the control unit as a phase difference target value;

target value modulating means for modulating the first target value by a predetermined modulation amount;

dielectric-constant computing means for computing a dielectric constant of the fuel on the basis of a first control output of the phase lock circuit, which corresponds to the first target value;

electric-conductivity computing means for computing an electric conductivity of the fuel based on an amount of shift between the first control output of the phase lock circuit, which corresponds to the first target value, and a second control output of the phase lock circuit, which corresponds to the modulated first target value;

mixing-ratio detecting means for detecting the fuel mixing ratio of the fuel from the computed dielectric constant and the computed electric conductivity.

5. A fuel mixing ratio detecting device comprising:

an LC resonance circuit having an electrostatic capacity detecting portion for detecting an electrostatic capacity of fuel and means electrically equivalent to a coil connected in parallel with the electrostatic capacity detecting portion;

a phase lock circuit having a voltage-controlled oscillator for generating a high-frequency signal having a frequency determined by a control voltage and for applying the generated high-frequency signal to the LC resonance circuit, a phase comparator for detecting a phase difference between a voltage and a current of the high-frequency signal applied to the LC resonance circuit, and a control unit for controlling the control voltage supplied to the voltage-controlled oscillator according to a difference between the phase difference detected by the phase comparator and a preliminarily set phase-difference target value;

target value setting means for setting a first target value in the control unit as a phase difference target value;

target value modulating means for modulating the first target value by a predetermined modulation amount;

dielectric-constant computing means for computing a dielectric constant of the fuel on the basis of a frequency of a high-frequency signal generated by the voltage-controlled oscillator correspondingly to the first target value;

electric-conductivity computing means for computing an electric conductivity of the fuel based on an amount of shift between the frequency of the high-frequency signal of the phase lock circuit, which corresponds to the first target value, and the frequency of the modulated high-frequency signal; and mixing-ratio detecting means for detecting the fuel mixing ratio of the fuel from the computed dielectric constant and the computed electric conductivity.

6. A fuel mixing ratio detecting device comprising:

an LC resonance circuit having an electrostatic capacity detecting portion for detecting an electrostatic capacity of fuel and means electrically equivalent to a coil connected in parallel with the electrostatic capacity detecting portion;

a phase lock circuit having a voltage-controlled oscillator for generating a high-frequency signal having a frequency determined by a control voltage and for applying the generated high-frequency signal to the LC resonance circuit, a phase comparator for detecting a phase difference between a voltage and a current of the high-frequency signal applied to the LC resonance circuit, and a control unit for controlling the control voltage for the voltage-controlled oscillator according to a difference between the phase difference detected by the phase comparator and a preliminarily set phase-difference target value;

target value setting means for setting a first target value in the control unit as a phase difference target value;

target value modulating means for modulating the first target value by a predetermined modulation amount;

dielectric-constant computing means for computing a dielectric constant of the fuel on the basis of a control voltage applied by the control unit to the voltage-controlled oscillator;

electric-conductivity computing means for computing an electric conductivity of the fuel based on an amount of shift between a first control output of the phase lock circuit, which corresponds to the first target value, and a second control output of the phase lock circuit, which corresponds to the modulated first target value; and mixing-ratio detecting means for detecting the fuel mixing ratio of the fuel from the computed dielectric constant and the computed electric conductivity.

7. The fuel mixing ratio detecting device according to claim 1, 2, 3, 4, 5 or 6, which further comprises dielectric-constant correcting means for correcting the dielectric constant, which is computed by the dielectric constant computing means, based on the amount of shift.

8. A fuel mixing ratio detecting device comprising:

an LC resonance circuit having an electrostatic capacity detecting portion for detecting an electrostatic capacity of fuel and means electrically equivalent to a coil connected in parallel with the electrostatic capacity detecting portion;

a phase lock circuit having a voltage-controlled oscillator for generating a high-frequency signal having a frequency determined by a control voltage and for applying the generated high-frequency signal to the LC resonance circuit, a phase comparator for detecting a phase difference between a voltage and a current of the high-frequency signal applied to the LC resonance circuit, and a control unit for controlling the control voltage supplied to the voltage-controlled oscillator according to a difference between the phase difference detected by the phase comparator and a preliminarily set phase-difference target value;

target value setting means for setting a first target value in the control unit as a phase difference target value of 0°;

dielectric-constant computing means for computing a dielectric constant of the fuel on the basis of a frequency of a high-frequency signal outputted from the voltage-controlled oscillator, which corresponds to the phase difference target value of 0°;

impedance detecting means for detecting an impedance of the LC resonance circuit when the phase difference target value is set to 0°;

electric-conductivity computing means for computing an electric conductivity of the fuel according to the detected impedance; and mixing-ratio detecting means for detecting a fuel mixing ratio of the fuel from the computed dielectric constant and the computed electric conductivity.

9. The fuel mixing ratio detecting device according to claim 8, further comprising dielectric-constant correcting means for correcting the dielectric constant, which is computed by the dielectric constant computing means, based on the impedance of the LC resonance circuit, which is detected by the impedance detecting means.

10. The fuel mixing ratio detecting device according to claim 8, further comprising applied-signal control means for changing a signal level of the high-frequency signal, which is applied to the LC resonance circuit, based on an output of the impedance detecting means.

* * * * *